(12) United States Patent
Tanaka

(10) Patent No.: US 7,668,290 B2
(45) Date of Patent: Feb. 23, 2010

(54) X-RAY DIAGNOSTIC SYSTEM

(75) Inventor: Manabu Tanaka, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 12/051,365

(22) Filed: Mar. 19, 2008

(65) Prior Publication Data

US 2008/0232548 A1   Sep. 25, 2008

(30) Foreign Application Priority Data

Mar. 20, 2007   (JP) .............................. 2007-072870

(51) Int. Cl.
*G01N 23/04* (2006.01)
(52) U.S. Cl. .......................................... 378/62; 378/95
(58) Field of Classification Search ............. 378/62–63, 378/98, 95, 96, 98.2, 98.8
See application file for complete search history.

(56) References Cited

U.S. PATENT DOCUMENTS

2001/0012328 A1*  8/2001  Koppe et al. ................... 378/62
2007/0195932 A1*  8/2007  Nakaura et al. ........... 378/98.12

FOREIGN PATENT DOCUMENTS

JP        2001-149360        6/2001

* cited by examiner

*Primary Examiner*—Hoon Song
(74) *Attorney, Agent, or Firm*—Oblon, Spivak, McClelland, Maier & Neustadt, L.L.P.

(57) ABSTRACT

An X-ray diagnostic system has a display unit, a selection unit, a calculation unit and an imaging execution unit. The display unit displays images of a plurality of frames collected by a predetermined frame rate about an object. The selection unit selects an image of a particular frame from the images of the frames displayed on the display unit. The calculation unit calculates a delay time to the particular frame selected by the selection unit based on the frame rate. The imaging execution unit executes an imaging based on the delay time calculated by the calculation unit.

18 Claims, 22 Drawing Sheets

X-RAY DIAGNOSTIC SYSTEM

BACKGROUND OF THE INVENTION

1. Field of the Invention

The present invention relates to a technology for generating and displaying angiogram image data, and more particularly, to an X-ray diagnostic system for generating and displaying 3D (three-dimensional) angiogram image data.

2. Description of the Related Art

There is known an X-ray diagnostic system composed of, for example, an X-ray tube and a flat panel detector (FPD) (or an image intensifier (I. I.)) disposed to both the ends of an approximately C-shaped supporter (C-arm) and an image processing device to image a blood vessel whose contrast is emphasized by a contrast medium. Generally, the X-ray diagnostic system is also called an angio apparatus and a 3D angio apparatus which permit a doctor to diagnose and treat (examine) a patient and to perform X-ray imaging by inserting a catheter into a patient.

The X-ray diagnostic system employs a method of rotation DSA (digital subtraction angiography) imaging. In the rotation DSA, first, mask images of a particular region (affected area) of the patient are collected from many different directions by rotating the C-arm in a necessary direction within the range of projection angle necessary to reconstruct the mask images to a 3D image. After the contrast medium is injected into the particular region of the patient, contrast images of the particular region are collected from many different directions by rotating the C-arm in a direction opposite to that when the mask images are collected (may be the same direction as that when the mask images are collected), and the rotation DSA imaging is performed. Then, a subtraction processing is performed to obtain the difference between 2D image data having projection angles corresponding to each other, and the 2D image data is reconstructed to 3D image, and the 3D image is displayed.

To obtain an excellent angiogram image data by the rotation DSA imaging, a timing at which the contrast of an imaging region is enhanced and the amount of the contrast medium are important factors. These factors depend on a position of a catheter, a region to be imaged (position of a region of interest) and a blood velocity, which is different depending on a patient. However, in actual 3D imaging, a predetermined delay time, which is determined based on experience values of a hospital using an apparatus, is often employed and applied to all the patients. As a result, the filled amount of a contrast medium in the interest region of a contrast image of a first frame, the filled amount of the contrast medium in the interest region of a final frame, and the amount of the contrast medium injected into a venous layer are not optimum, and thus 3D image data suitable for diagnosis cannot be always obtained.

To cope with this problem, there is disclosed a technology for setting an interest region as ROI (region interest) in previously collected images, injecting a contrast medium after mask imaging is performed, and automatically performing a fluoroscopy during a period until contrast imaging is started after the contrast medium is injected (for example, Japanese Patent Application Publication No. 2001-149360). In this technology, since an image level changes when the contrast medium flows into ROI, the contrast imaging is started by sensing the change of the image level.

Although the delay time is different depending on an examiner (position of catheter), a region, a patient (blood velocity), a symptom, and the like, when the technology disclosed in Japanese Patent Application Publication No. 2001-149360 is not used, since 3D imaging is performed using the predetermined delay time determined based on the experience values of the hospital, a 3D image suitable for diagnosis cannot be generated.

In contrast, when the technology disclosed in Japanese Patent Application Publication No. 2001-149360 is used, since the fluoroscopy must be continued during the period until the contrast imaging is started from the start of injection of the contrast medium after the mask imaging is performed, a problem arises in that the amount of exposure of a patient to an X-ray is increased. Accordingly, it is difficult to practically use the technology disclosed in Japanese Patent Application Publication No. 2001-149360.

SUMMARY OF THE INVENTION

The present invention has taken into consideration the above-described problems and it is an object of the present invention to provide an X-ray diagnostic system which an accuracy of an X-ray diagnosis can be improved while reducing an unnecessary exposure of the patient to an X-ray.

To solve the above-described problems, the present invention provides an X-ray diagnostic system comprising: a display unit configured to display images of a plurality of frames collected by a predetermined frame rate about an object; a selection unit configured to select an image of a particular frame from the images of the frames displayed on the display unit; a calculation unit configured to calculate a delay time to the particular frame selected by the selection unit based on the frame rate; and an imaging execution unit configured to execute an imaging based on the delay time calculated by the calculation unit.

DESCRIPTION OF THE PREFERRED EMBODIMENTS

Embodiments of an X-ray diagnostic system according to the present invention will be explained referring to the accompanying drawings.

An angio apparatus as the X-ray diagnostic system has a DSA (digital subtraction angiography) imaging mode. In the DSA imaging mode, image data of a difference image (2D-DSA image), which is a 2D angiogram, can be generated by subjecting the image data of a 2D (2-dimensional) X-ray fluoroscopic image (mask image) which does not include the image of a contrast medium and image data of a 2D X-ray fluoroscopic image (contrast image or live image) which includes the image of the contrast medium to a subtraction processing, and image data of the 2D-DSA image in on direction can displayed and stored.

Further, in the DSA imaging mode of the angio apparatus, rotation DSA imaging, which generates image data of a 3D-DSA image (rotation DSA image), can be performed by performing DSA imaging while rotating a C-arm at a high speed (for example, 40°/sec). That is, in the DSA imaging mode of the angio apparatus, the image data of a difference image (3D-DSA image), which is a 3D angiogram, is generated by performing 3D reconstruction based on the image data of multidirectional 2D-DSA images. According to the rotation DSA imaging, the image data of the 3D-DSA image can be instantly displayed and stored by injecting a contrast medium only once.

First Embodiment

Figure 1:
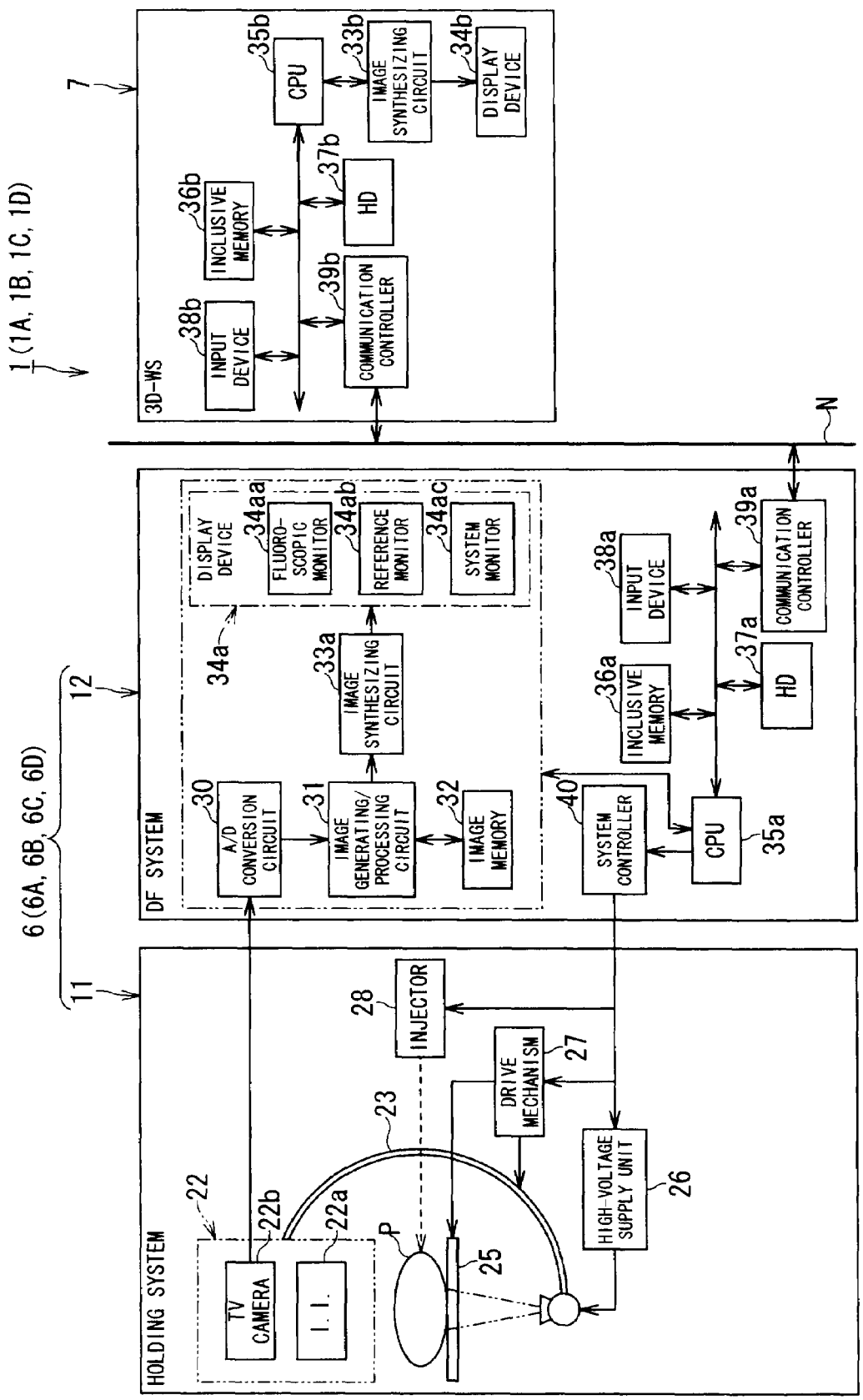
FIG. 1 is a schematic view showing a hardware arrangement of first-fifth embodiments of the X-ray diagnostic system according to the present invention.

FIG. 1 is a schematic view showing a hardware arrangement of a first embodiment of the X-ray diagnostic system according to the present invention.

FIG. 1 shows the X-ray diagnostic system 1 of the first embodiment. The X-ray diagnostic system 1 is composed of an angio apparatus 6 as the X-ray diagnosis apparatus and a 3D-WS (work station) 7 connected to the angio apparatus 6 through a network N so that the angio apparatus 6 can communicate with the 3D-WS (work station) 7 therethrough. The angio apparatus 6 is roughly composed of a holding system 11 and a DF (digital fluorography) system 12. Note that the 3D-WS7 is not a component indispensable to the X-ray diagnostic system 1.

The holding system 11 includes an X-ray tube 21, an X-ray detection unit 22, a C-arm 23, a table-top (catheter table) 25, a high-voltage supply unit 26, a drive mechanism 27, and an automatic contrast medium injection unit (injector) 28. Note that although the holding system 11 is explained as to an undertube type case in which the X-ray tube 21 is located under the table-top 25, an overtube type in which the X-ray tube 21 is located on the table-top 25 may be also employed. Further, an X-ray radiation field diaphragm, which is composed of a plurality of lead blades, and a compensation filter, which is composed of silicon rubber and the like for attenuating a predetermined amount of a radiated X-ray to prevent halation, may be disposed on the X-ray outgoing side of the X-ray tube 21.

The X-ray tube 21 is disposed to one end of the C-arm 23, supplied with high voltage power from the high-voltage supply unit 26, and exposes an object (patient) P with an X-ray according to the condition of the high voltage power.

The X-ray detection unit 22 is disposed to the other end of the C-arm 23 on the outgoing side of the X-ray tube 21 and detects the X-ray passing through the patient P. The X-ray detection unit 22 functions as I. I. (image intensifier)-TV system and roughly includes an I. I. 22a and a TV camera 22b.

The I. I. 22a converts the X-ray passing through the patient P into visible light and further causes the visible light to form projection data having good sensitivity by multiplying the luminance of the visible light in a light-electron-light conversion process. The TV camera 22b converts the optical projection data into an electronic signal using a CCD (charge coupled device) imaging device.

Note that the X-ray detection unit 22 may include a flat panel detector (FPD). When the X-ray detection unit 22 has the flat panel detector, the X-rays which were incident on the flat panel detector are converted into an electric charge in an X-rays conversion unit such as amorphous selenium (a-Se, not shown).

The C-arm 23 supports the X-ray tube 21 on the one end thereof and the X-ray detection unit 22 on the other end thereof so that the X-ray tube 21 and the X-ray detection unit 22 are disposed in confrontation with each other around the patient P. The amount and the timing of movement and the moving velocity of the C-arm 23 are controlled by the drive mechanism 27.

The table-top 25 places the patient P thereon.

The high-voltage supply unit 26 supplies the high voltage power to the X-ray tube 21 under the control of the DF system 12.

The drive mechanism 27 moves the C-arm 23 in a left anterior oblique view (LAO) direction and a right anterior oblique view (RAO) direction and rotates the C-arm 23 in a cranial view (CRA) direction and a caudal view (CAU) direction under the control of the DF system 12. Since the circular movement and the rotational movement of the C-arm 23 is controlled by the drive mechanism 27, DSA imaging for obtaining image data from one direction and rotation DSA imaging for obtaining from many different directions can be realized.

The drive mechanism 27 moves the C-arm 23 in parallel with the body axis direction of the patient P and integrally raises and falls the C-arm 23 and the table-top 25 under the control of the DF system 12. Further, the drive mechanism 27 linearly moves the C-arm 23 in the body axis direction of the patient P under the control of the DF system 12 to image the patient P by moving the X-ray tube 21 and the X-ray detection unit 22 in the body axis direction of the patient P. In addition to the above-mentioned movements, the drive mechanism 27 moves the table-top 25 in an up/down direction, a left right direction, and the body axis direction under the control of the DF system 12.

The injector 28 is a unit for injecting a contrast medium into a catheter (catheter tube, not shown) inserted into an affected area of the patient P under the control of the DF system 12.

According to the holding system 11 having the C-arm structure, an examiner such as a doctor and the like can directly touch the patient P making use of an open end of the C-arm 23 as a component of the holding system 11, the examiner can perform X-ray imaging by enhancing the contrast of a blood vessel at the same time the examiner performs an operation or an examination such as insertion of a catheter into the body of the patient P and the like. Accordingly, the angio apparatus 6 having the C-arm structure can perform IVR (interventional radiology) and the like which require a complex catheter manipulation and the like.

In contrast, the DF system 12 is basically composed of a computer and can make mutual communication with a network N such as a backbone LAN (local area network) and the like of a hospital. The DF system 12 is roughly composed of hardware of an A/D (analog to digital) conversion circuit 30, an image generating/processing circuit 31, an image memory 32, an image synthesizing circuit 33a, a display device 34a, a CPU (central processing unit) 35a, an inclusive memory 36a, an HD (hard disc) 37a, an input device 38a, a communication controller 39a, a system controller 40, and the like. The CPU 35a is mutually connected to the respective hardware components constituting the DF system 12 through a bus as a common signal transmission path. Note that the DF system 12 may include a recording medium drive (not shown).

The A/D conversion circuit 30 converts a time-sequential analog signal (video signal) output from the X-ray detection unit 22 into a digital signal.

The image generating/processing circuit 31 subjects the digital signal of projection data output from the A/D conversion circuit 30 to a logarithm conversion processing (LOG processing) and to an addition processing when necessary, generates image data (the image data of a mask image and the image data of a contrast image) of a frame unit, and stores the image data to the image memory 32 under the control of the CPU 35a. Further, the image generating/processing circuit 31 subjects the image data of the frame unit to an image processing and stores the image data subjected to the image processing to the image memory 32. Exemplified as the image processing are enlargement/gradation/space filter processing to the image data, a minimum value/maximum value trace processing to the image data accumulated time-sequentially, a subtraction processing, an addition processing for eliminating noise, and the like. Note that the image data subjected to the image processing by the image generating/processing circuit 31 is output to the image synthesizing circuit 33a as well as stored to a storage unit such as the image memory 32 and the like.

The image memory 32 stores the image data output from the image generating/processing circuit 31 under the control of the CPU 35a.

The image synthesizing circuit 33a synthesizes the image data output from the image generating/processing circuit 31 together with the character information of various types of parameters, graduations, and the like and outputs the image data to the display device 34a as a video signal. Further, the image synthesizing circuit 33a synthesizes the image data of the 2D-DSA image subjected to the subtraction processing by the image generating/processing circuit 31 together with the character information of various types of parameters, graduations, and the like and outputs the image data to the display device 34a as a video signal.

Figure 2:
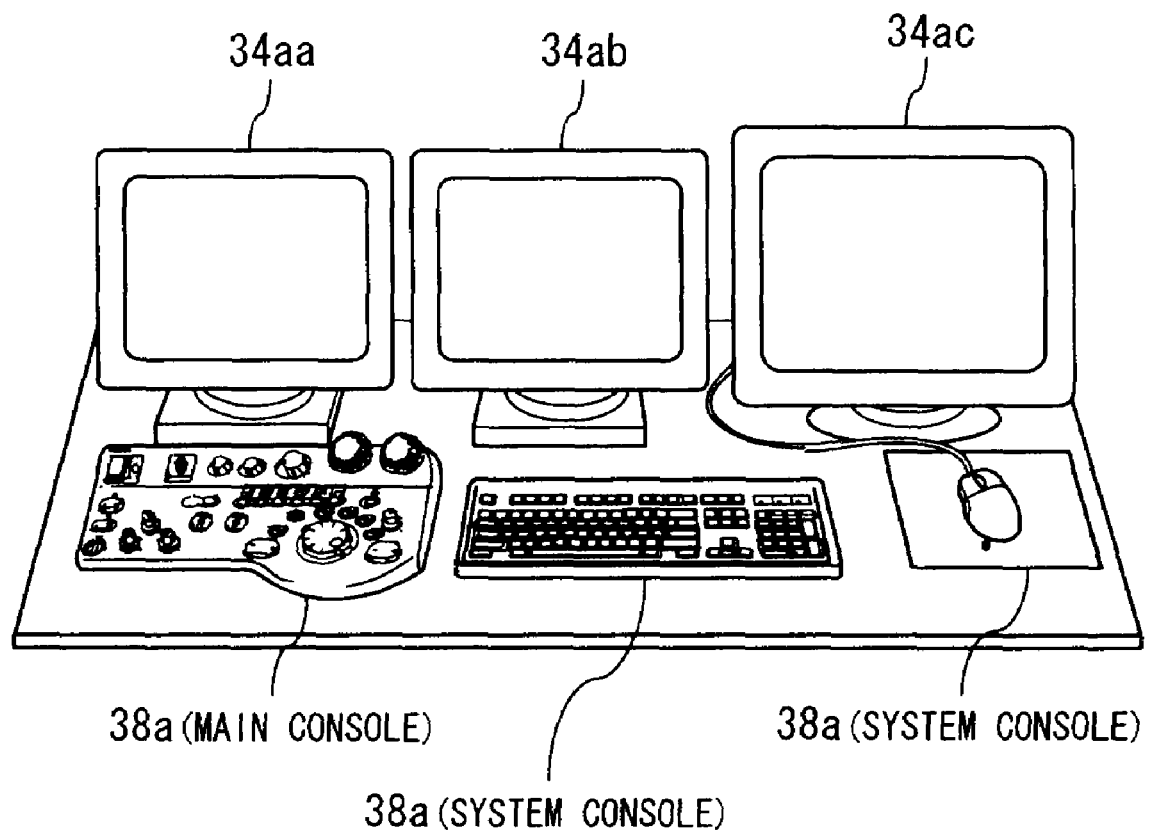
FIG. 2 is a view showing an example of a layout of a display device.

FIG. 2 is a view showing an example of a layout of the display device 34a.

The display device 34a is composed of a fluoroscopic monitor 34aa, a reference monitor 34ab, and a system monitor 34ac.

Further, the display device 34a includes a display image memory such as VRAM (video random access memory, not shown) and the like, a D/A (digital to analog) converter, and a display circuit. Since image data and the like are developed to the VRAM, which develops image data that is intended to be displayed, under the control of the CPU 35a, the image data such as the 2D-DSA image and the like is displayed on the display device 34a.

The fluoroscopic monitor 34aa mainly displays the image data of a live image. The fluoroscopic monitor 34aa displays the image data of a mask image and the image data of a contrast image output from the image synthesizing circuit 33a as the live image.

The reference monitor 34ab mainly displays the image data of a still image and the image data of a reproduced image. Further, the reference monitor 34ab also displays the image data of the 2D-DSA image output from the image synthesizing circuit 33a.

The system monitor 34ac mainly displays data for controlling the holding system 11, collecting of data and so on such as data for switching FOV (field of view), and the like.

When the examiner inputs a command by manipulating the input device 38a, the CPU 35a executes a program stored to the inclusive memory 36a. Otherwise, the CPU 35a loads a program stored to the HD 37a, a program, which is transferred from the network N, received by the communication controller 39a, and installed on the HD 37a, or a program, which is read out from a recording medium mounted on the recording medium drive (not shown) and installed on the HD 37a, on the inclusive memory 36a and executes the program.

The inclusive memory 36a is a storage unit which also functions as ROM (read only memory), RAM (random access memory), and the like and stores IPL (initial program loading), BIOS (basic input/output system), and data, and temporarily stores a work memory and data of the CPU 35a.

The HD 37a is composed of a non-volatile disc and the like. The HD 37a is a storage unit for storing data such as data of a program (including OS (operating system) in addition to application program) installed on the DF system 12, pilot image data to mention later and so on according to control by a HDD (hard disk drive, not shown). Further, GUI (graphical user interface), which can employ many graphics to display information to a user and can cause the input device 38a to perform a basic manipulation may be provided as OS.

Further, as the storage device, RAID (redundant array of independent disks, not shown) that can control these whole as one HDD may be adopted by arranging plural physics drives such as HDDs. In this case, the RAID controller (not shown) forms a logical drive by HDDs and controls the reading and writing for the logical drive.

A keyboard, a mouse, and the like, which can be manipulated by the examiner, are exemplified as the input device 38a, and an input signal according to manipulation is supplied to the CPU 35a. The input device 38a is roughly composed of a main console and a system console.

The communication controller 39a performs a communication control according to respective standards. The communication controller 39a has a function capable of being connected to the network N through a network cable such as LAN cable, thereby the angio apparatus 6 can be connected to the network N from the communication controller 39a.

The system controller 40 includes a CPU and a memory both of which are not shown. The system controller 40 controls the operations of the high-voltage supply unit 26, the drive mechanism 27 and the injector 28, and the like of the holding system 11 in response to an instruction from the CPU 35a.

Further, the 3D-WS7 of the X-ray diagnostic system 10 is basically composed of a computer and includes an image synthesizing circuit 33b, a display device 34b, a CPU 35b, an inclusive memory 36b, an HD 37b, an input device 38b, a communication controller 39b, and the like. The CPU 35b is mutually connected to the respective hardware components constituting the 3D-WS7 through the bus as the common signal transmission path. Note that the 3D-WS7 may include a recording medium dive (not shown).

When a command is input by manipulating the input device 38b, the CPU 35b executes a program stored to the inclusive memory 36b. Otherwise, the CPU 35b loads a program stored to the HD 37b, a program, which is transferred from the network N, received by the communication controller 39b, and installed on the HD 37b, or a program, which is read out from a recording medium mounted on the recording medium drive (not shown) and installed on the HD 37b, on the inclusive memory 36b and executes the program.

The inclusive memory 36b is a storage unit which also functions as ROM, RAM, and the like and stores IPL, BIOS, and data and temporarily stores a work memory and data of the CPU 35b.

The HD 37b is composed of a non-volatile disc and the like. The HD 37b is a storage unit for storing a program installed on the 3D-WS7 and data. Further, GUI, which can employ many graphics to display information to a user and can cause the input device 38b to perform a basic manipulation may be provided as OS.

A keyboard, a mouse, and the like, which can be manipulated by the examiner are exemplified as the input device 38b, and an input signal according to manipulation is supplied to the CPU 35b.

The communication controller 39b performs a communication control according to the respective standards. The communication controller 39b has a function capable of being connected to the network N through the network cable, thereby the 3D-WS7 can be connected to the network N from the communication controller 39b.

Figure 3:
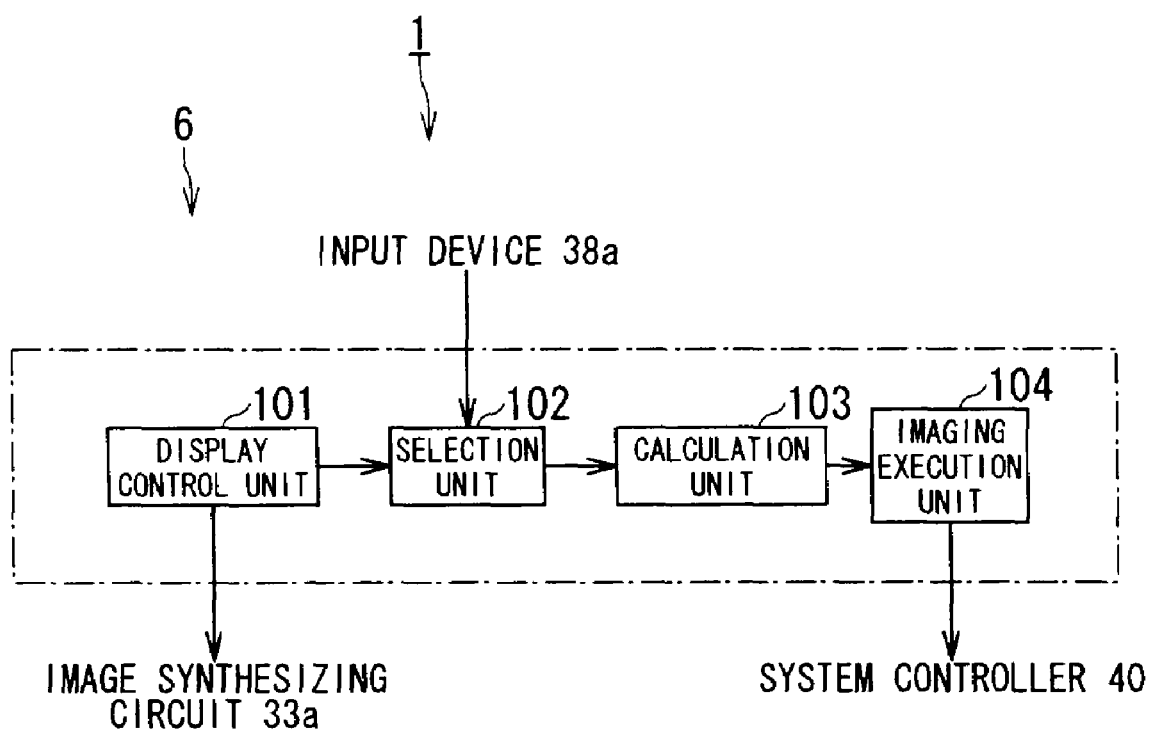
FIG. 3 is a block diagram showing a function of the first embodiment of the X-ray diagnostic system according to the present invention.

FIG. 3 is a block diagram showing a function of the first embodiment of the X-ray diagnostic system according to the present invention.

FIG. 3 shows a function of the angio apparatus 6 constituting the X-ray diagnostic system 1. As shown in FIG. 3, when the CPU 35a shown in FIG. 1 executes the program, the angio apparatus 6 functions as a display control unit 101, a selection unit 102, a calculation unit 103, and an imaging execution unit 104. Note that although a case that the display control unit 101, the selection unit 102, the calculation unit 103, and the imaging execution unit 104 are constructed by software will be explained in the embodiment, the embodiment is not limited thereto, and they may be entirely or partly constructed by hardware composed of a circuit and the like.

The display control unit 101 has a function for displaying images of a plurality of frames about an object, the images collected by a predetermined frame rate. The images, which are displayed on the display control unit 101, may be the images collected by a series of examination before the imaging execution unit 104 collects images or may be the images collected by another examination before the imaging execution unit 104 collects the images. In the latter case, it is assumed that the images of a patient, who is the same as the patient whose images are collected by the imaging execution unit 104, are previously collected.

The selection unit 102 has a function for selecting an image of a particular frame from the images of the frames displayed on the display control unit 101 in response to a signal input from the input device 38a.

The calculation unit 103 has a function for calculating a delay time up to the particular frame selected by the selection unit 102 based on the frame rate when the collected images are collected.

The imaging execution unit 104 has a function for executing imaging by controlling the system controller 40 based on the delay time calculated by the calculation unit 103. The imaging performed by the imaging execution unit 104 may be imaging for obtaining 2D-DSA images from many different directions to generate a 3D-DSA image or may be imaging for obtaining a 2D-DSA image in one direction.

When the X-ray diagnostic system 1 has the 3D-WS7, the 3D-WS7 can reconstruct the 3D-DSA image based on the 2D-DSA image from many different directions supplied from the angio apparatus 6.

According to the X-ray diagnostic system 1 of the embodiment, a DSA image having improved S/N (signal/noise) and a small amount of artifact can be generated and displayed by optimizing the delay time while reducing unnecessary exposure of the patient P to the X-ray when the imaging is performed by the imaging execution unit 104. More specifically, according to the X-ray diagnostic system 1 of the embodiment, the accuracy of the X-ray diagnosis can be improved while reducing the unnecessary exposure of the patient P to the X-ray.

Second Embodiment

Figure 4:
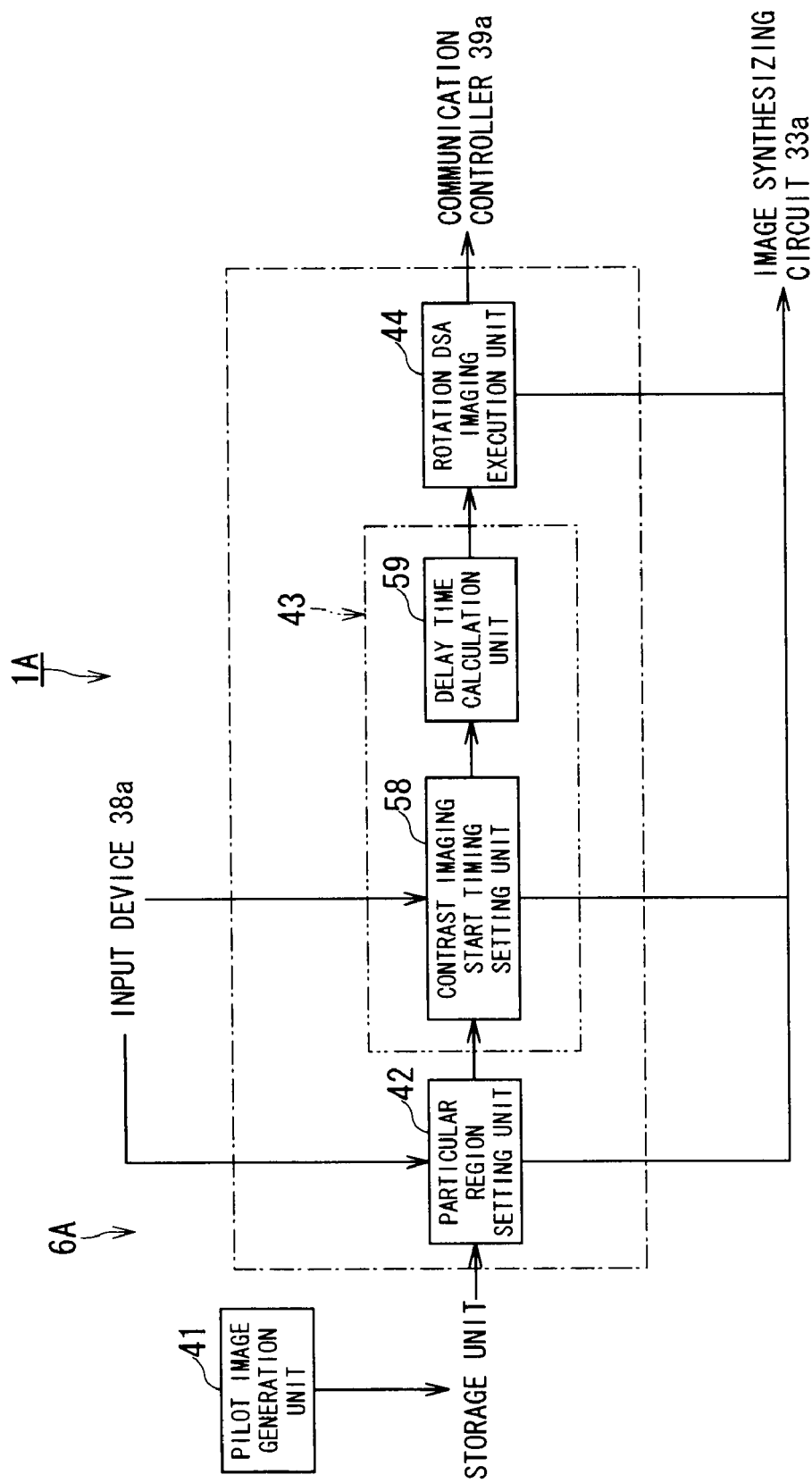
FIG. 4 is a block diagram showing a part of a function of the second embodiment of the X-ray diagnostic system according to the present invention.
Figure 5:
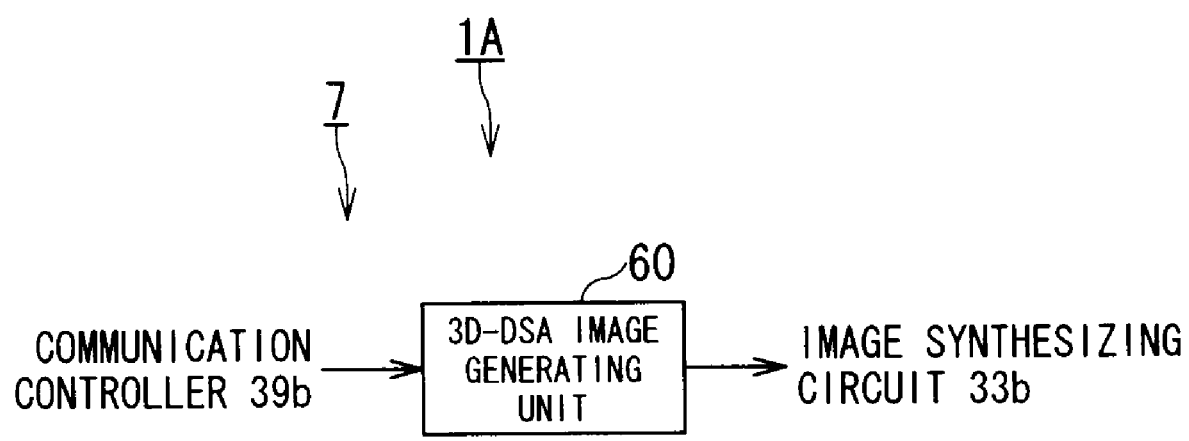
FIG. 5 is a block diagram showing a part of a function of the second embodiment of the X-ray diagnostic system according to the present invention.

As shown in FIGS. 1, 4, and 5, an X-ray diagnostic system 1A of a second embodiment is composed of an angio apparatus 6A functioning as an X-ray diagnosis device and a 3D-WS7. Since the hardware arrangement of the X-ray diagnostic system 1A of the second embodiment is the same as that of the X-ray diagnostic system 1 of the first embodiment shown in FIG. 1, the explanation thereof is omitted. In contrast, the software arrangement of the X-ray diagnostic system 1A of the second embodiment will be explained below.

FIGS. 4 and 5 are block diagrams showing a function of the second embodiment of the X-ray diagnostic system according to the present invention.

FIG. 4 shows a function of the angio apparatus 6A in the function of the X-ray diagnostic system IA. In contrast, FIG. 5 shows a function of the 3D-WS7 in the function of the X-ray diagnostic system 1A.

As shown in FIG. 4, when a CPU 35a (shown in FIG. 1) executes a program, the angio apparatus 6A functions as a pilot image generation unit 41, a particular region setting unit 42, a delay time setting unit 43, and a rotation DSA imaging execution unit 44 in a series of examinations. Further, the delay time setting unit 43 has a contrast imaging start timing setting unit 58 and a delay time calculation unit 59. Note that the pilot image generation unit 41 is not a component indispensable to the angio apparatus 6A. Although a case that the pilot image generation unit 41, the particular region setting unit 42, the delay time setting unit 43, the rotation DSA imaging execution unit 44, are constructed by software is explained in the embodiment, the embodiment is not limited thereto, and they may be entirely or partly constructed by hardware composed of a circuit and the like.

The pilot image generation unit 41 has a function for generating the image data of an angiogram (hereinafter, referred to as a "pilot image") for generating a delay time employed when 3D imaging is performed to a particular region of a patient P. Although a case that the image data of a 2D-DSA image which is a 2D angiogram is employed as the pilot image is explained below, this may be a case that the image data of a 3D-DSA image which is a 3D angiogram is employed. The pilot image generation unit 41 generates the image data of mask images and the image data of contrast images from one direction of a plurality of regions of a patient P before 3D imaging is performed to the particular region and further generates the image data of pilot images from one direction based on the above image data.

Specifically, the pilot image generation unit 41 generates the image data of the mask images from one direction of the respective regions of the patient P by performing mask imaging by controlling a system controller 40 (shown in FIG. 1) and stores the data to a storage unit such as an image memory 32 (shown in FIG. 1) and the like. Further, after the pilot image generation unit 41 automatically injects a contrast medium from an injector 28 by controlling the system controller 40, it generates the image data of the contrast images of the respective region of the patient P by performing contrast imaging to the regions corresponding to the mask images employing the delay time set to a default value ("$T_0$" to be described later) and stores the image data to the storage unit such as the image memory 32 (shown in FIG. 1) and the like. Note that the default value may be set to each region as the delay time.

Further, the pilot image generation unit 41 generates the image data of pilot images which are 2D angiograms by a subtraction processing based on the mask images and the contrast images (live images) by controlling an image generating/processing circuit 31 and the image memory 32 (both shown in FIG. 1). Note that pilot images are stored to the storage unit such as the HD 37a (shown in FIG. 1) and the like. Since the pilot image generation unit 41 generates the pilot images of the plurality of regions of the patient P, the storage unit stores the pilot image of each of the plurality of regions.

The particular region setting unit 42 has a function for reading out the pilot image of each region stored to the storage unit such as the HD 37a and the like and displaying the pilot image of each region on a display device 34a, for example, a reference monitor 34ab through an image synthesizing circuit 33a. In this case, it is sufficient that the particular region setting unit 42 displays only the pilot image of a predetermined frame in each region on the reference monitor 34ab. Further, the particular region setting unit 42 has a function for setting the particular region to which the 3D imaging is performed based on the pilot image selected from the pilot images of the respective regions displayed on the reference monitor 34ab (shown in FIG. 1).

The contrast imaging start timing setting unit 58 of the delay time setting unit 43 has a function for displaying the pilot images of the respective frames corresponding to the particular region set by the particular region setting unit 42 on the display device 34a, for example, the reference monitor 34ab (shown in FIG. 1) through the image synthesizing circuit 33a. Further, the contrast imaging start timing setting unit 58 has a function for setting a contrast imaging start timing suitable for the start of the contrast imaging for performing the 3D imaging of the particular region based on the particular frame selected from the pilot images of the respective frames corresponding to the particular region displayed on the reference monitor 34ab and a frame rate employed when the pilot image (contrast image included in the pilot image) of the particular region is generated. Specifically, the contrast imaging start timing setting unit 58 sets the contrast imaging start timing ($n_s/R$) based on the pilot image of an $n_s$-th ($n_s=1, 2, 3, \ldots$) frame selected from the pilot images of the respective frames corresponding to the particular region and the frame rate R employed when the pilot images of the particular region are generated.

The delay time calculation unit 59 has a function for calculating a delay time $T_1$, which employed when the 3D imaging (contrast imaging included in 3D imaging) of the particular region is performed, based on the contrast imaging start timing ($n_s/R$) set by the contrast imaging start timing setting unit 58 and a delay time $T_0$, employed when the pilot images of the particular region set by the particular region setting unit 42 are generated. For example, the delay time calculation unit 59 calculates the delay time $T_1$, which is employed when the 3D imaging of the particular region is performed, using a following equation (1).

$$T_1 = T_0 + n_s/R \tag{1}$$

Figure 6:
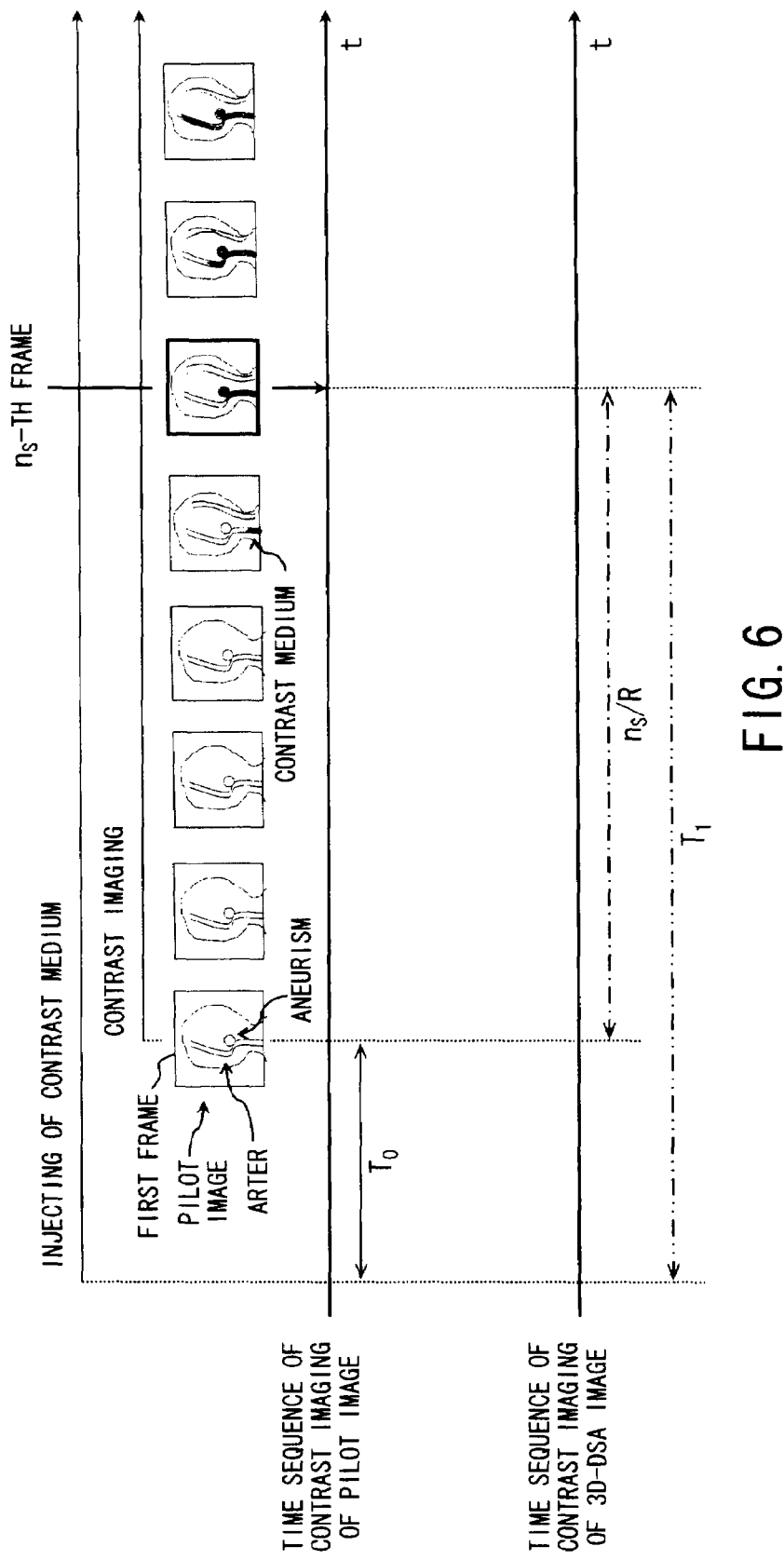
FIG. 6 is a view explaining an equation (1) for calculating a delay time employed when a 3D imaging of a particular region is performed.

FIG. 6 is a view explaining the equation (1) for calculating the delay time $T_1$ employed when the 3D imaging of the particular region is performed.

An upper part of FIG. 6 shows a time sequence (t) of the contrast imaging of the pilot images performed to the particular region generated by the pilot image generation unit 41 and the pilot images. In the contrast imaging of the pilot images, first, the contrast medium starts to be injected at a certain timing, and then the contrast imaging is automatically started and the pilot images are generated after the delay time $T_0$ set to the default value passes. The delay time $T_0$ employed in the contrast imaging is applied to the image data according to, for example, DICOM (digital imaging and communication in medicine) standard. Note that the DICOM standard is standardized in the United States to provide common medical information.

A lower part of FIG. 6 shows a time-sequence (t) designed based on the upper part and shows the time sequence (t) of the contrast imaging included in the 3D imaging performed to the particular region. The delay time $T_1$, which employed when the contrast imaging is performed, is calculated by the equation (1) based on the contrast imaging start timing ($n_s/R$) and the delay time $T_0$.

The rotation DSA imaging execution unit 44 shown in FIG. 4 has a function for generating the image data of the mask images of the particular region set by performing the mask imaging from many different directions to the particular region set by the particular region setting unit 42 by controlling the system controller 40 (shown in FIG. 1) and storing the image data to the storage unit such as the image memory 32 (shown in FIG. 1) and the like. Further, the rotation DSA imaging execution unit 44 has a function for performing the contrast imaging from many different directions employing the delay time $T_1$ set by the delay time setting unit 43 by controlling the system controller 40, generating the image data of the contrast images of the particular region, and storing the image data to the storage unit such as the image memory 32 (shown in FIG. 1) and the like. The rotation DSA imaging execution unit 44 causes the display device 34a, for example, a fluoroscopic monitor 34aa (shown in FIG. 1) to display the mask images and the contrast images as the live images through an image synthesizing circuit 33a.

Further, the rotation DSA imaging execution unit 44 has a function for calculating image data used to reconstruct a 3D-DSA image of the particular region based on the mask images and the contrast images from many different directions by controlling the image generating/processing circuit 31 and the image memory 32 (both of them shown in FIG. 1). The image data generated by the rotation DSA imaging execution unit 44 is transferred to the 3D-WS7 through a communication controller 39a.

As shown in FIG. 5, when the CPU 35b (shown in FIG. 1) executes the program, the 3D-WS7 functions as a 3D-DSA image generating unit 60. Note that although a case that the 3D-DSA image generating unit 60 is constructed by software will be explained in the embodiment, the embodiment is not limited thereto, and the 3D-DSA image generating unit 60 may be constructed by hardware composed of a circuit and the like. Further, although a case that the 3D-DSA image generating unit 60 is disposed to the 3D-WS7 is explained in the embodiment, the 3D-DSA image generating unit 60 may be disposed to a DF system 12 of the angio apparatus 6A.

The 3D-DSA image generating unit 60 has a function for generating the image data of the 3D-DSA image of the particular region by performing a 3D reconstruction processing to the image data transferred from the angio apparatus 6A through the communication controller 39b. The 3D-DSA image generating unit 60 causes the display device 34b (shown in FIG. 1) to display the 3D-DSA image through the image synthesizing circuit 33b.

Figure 7:
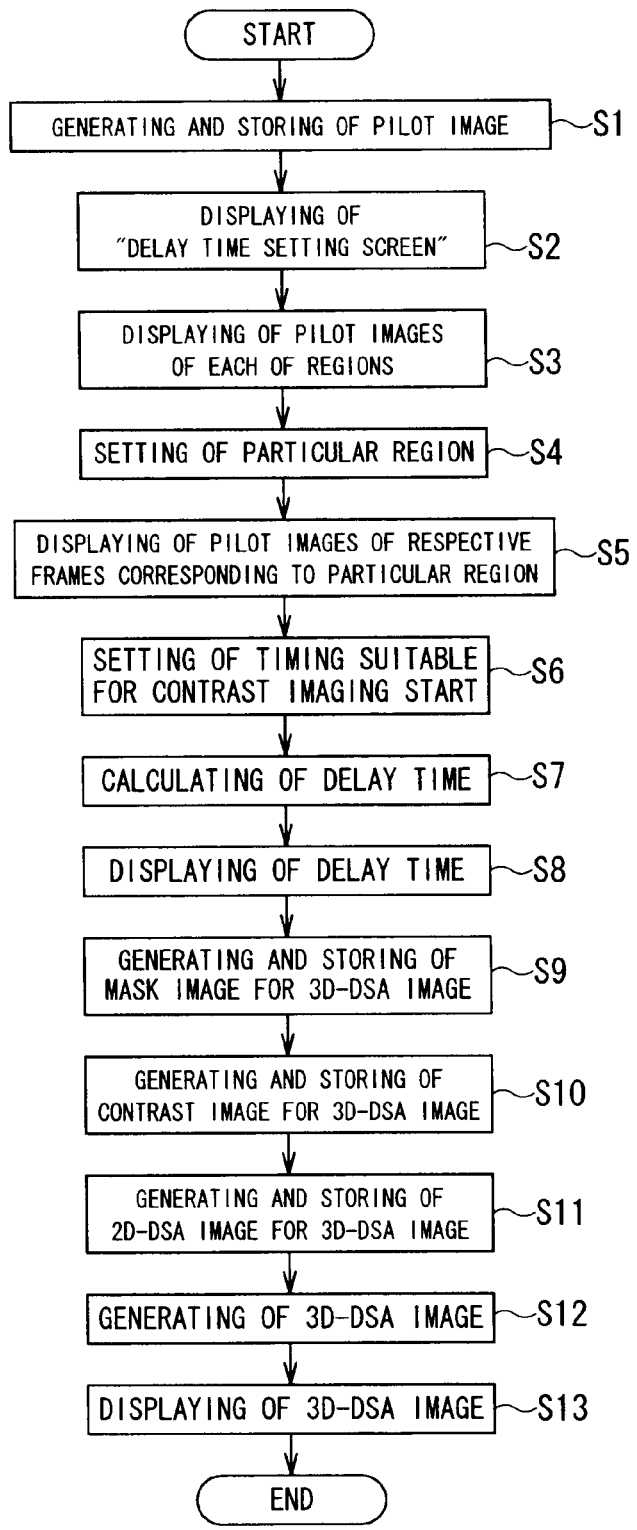
FIG. 7 is a flowchart showing an operation of the diagnostic system of the second embodiment.
Figure 8:
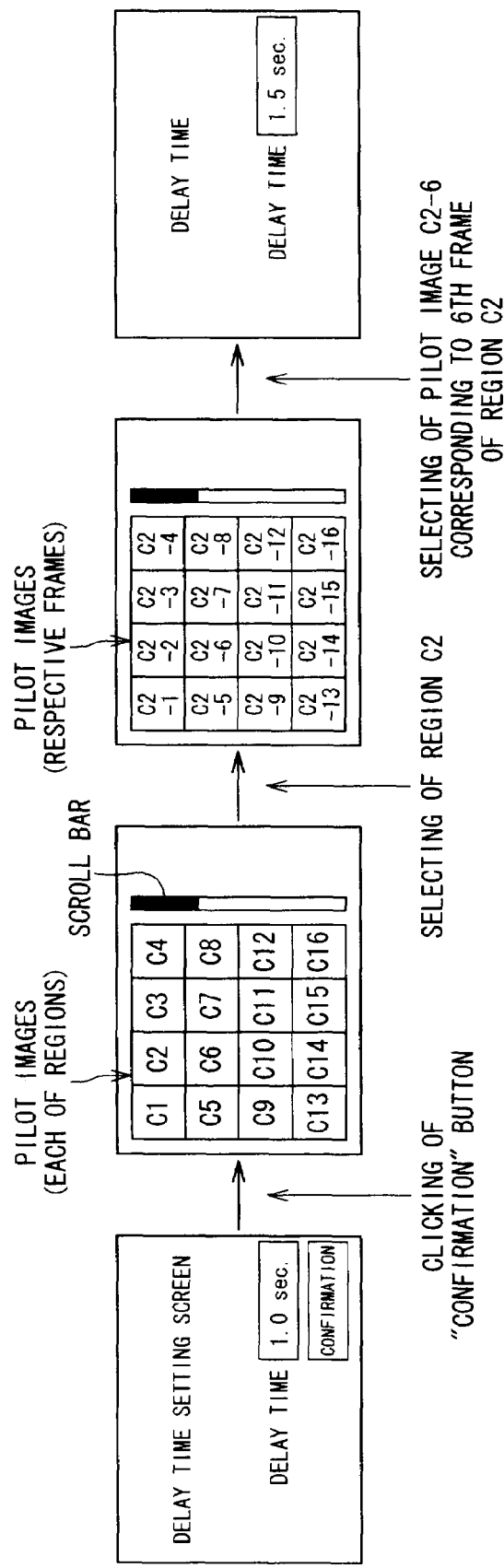
FIG. 8 is a diagram showing a "delay time setting screen"

Subsequently, an operation of the diagnostic system 1A of the embodiment will be explained using a flowchart shown in FIG. 7. Further, FIG. 8 shows the display screens which are appropriately displayed on the display device 34b of the 3D-WS7 according to the operation of the diagnostic system 1A.

First, a catheter is inserted into the body of the patient P placed on a table-top 25. When the CPU 35a of the angio apparatus 6A executes the program, the angio apparatus 6A performs mask imaging by controlling the system controller 40, generates the image data of mask images from one direction of the plurality of regions, and causes the storage unit such as the image memory 32 and the like to store the image data.

Further, the angio apparatus 6A starts to automatically inject a contrast medium from an injector 28 by controlling the system controller 40. After the delay time set to the default value passes from the start of injection of the contrast medium, the angio apparatus 6A automatically start contrast imaging. After the start of the contrast imaging, the image data of the contrast images from the one direction of the region corresponding to the mask images are generated and stored to the storage unit such as the image memory 32 and the like.

Note that when the image data of mask images and the image data of the contrast images of the plurality of regions are generated, the mask imaging and the contrast imaging may be repeated to each of the regions.

Next, the image data of the pilot images which are the 2D angiograms is generated and stored based on the mask images and the contrast images in the one direction by controlling the image generating/processing circuit 31, the image memory 32 and the HD 37a (step S1). At step S1, the pilot image is generated and stored to each of the plurality of regions by generating the mask images and the contrast images to the plurality of regions.

Next, when a 3D-DSA imaging program is selected, a "delay time setting screen" is displayed on the display device 34a, for example, a system monitor 34ac (step S2, screen of left edge in FIG. 8). The delay time set to the default value is displayed on the "delay time setting screen".

When an examiner clicks a "confirmation" button on the "delay time setting screen", the pilot image of each region which is generated and stored at step S1 is read out and displayed on the display device 34a, for example, on the reference monitor 34ab as a thumbnail image (step S3, second screen from left in FIG. 8). Further, the particular region to which the 3D imaging is performed is set based on the pilot images of the respective regions displayed on the reference monitor 34ab (step S4). Specifically, a region C2 as a the particular region is set by the examiner who selects the region C2 from the respective regions (region C1, C2, C3, ...) displayed on the reference monitor 34ab using an input device 38a.

Next, the pilot images of the respective frames corresponding to the particular region set at step S4 is time-sequentially displayed on the display device 34a, for example, on the reference monitor 34ab as thumbnail images (step S5, second screen from right in FIG. 8). Further, the pilot image of a, $n_s$-th frame corresponding to the start of the contrast imaging is selected based on the pilot images of the respective frames (first frame, second frame, third frame, ...) corresponds to the particular region displayed on the reference monitor 34ab. Specifically, the examiner selects the pilot image C2-6 of the $n_s$-th frame, for example, a sixth frame from the pilot images of the respective frames corresponding to the region C as the particular region using the input device 38a. Note that the examiner preferably selects a frame in which the contrast medium reaches an interest region (for example, a region where aneurism exists) when the 3D imaging is performed.

Further, the contrast imaging start timing suitable to start the contrast imaging is set based on the selected $n_s$-th frame and the frame rate employed when the pilot images of the particular region is generated (step S6).

Next, the delay time, which is employed when the 3D imaging of the particular region is performed, is calculated using the equation (1) based on the contrast imaging start timing set at step S6 and the delay time employed when the pilot image of the particular region is generated (step S7).

The delay time calculated at step S7 is displayed on the display device 34a, for example, on the system monitor 34ac (step S8, screen of right edge in FIG. 8). When the examiner pushes an imaging-start switch after a completion of preparations for the 3D imaging, the 3D imaging is started.

In the 3D imaging, first, the mask imaging is started by rotation DSA. In the mask imaging, the operations of a high-voltage supply unit 26 and a drive device 27 are controlled through the system controller 40, and an X-ray is radiated from an X-ray tube 21 to the particular region of the patient P from many different directions while moving a C-arm 23 to a position suitable for the mask imaging.

The image generating/processing circuit 31 generates the image data of the mask image of a frame unit based on the digitized projection data output from an X-ray detection unit 22 under the control of the CPU 35a and stores the image data to the image memory 32 as well as outputs it to the image synthesizing circuit 33a. The image generating/processing circuit 31 subjects the image data of the mask images stored to the image memory 32 to an image processing when necessary under the control of the CPU 35a and stores the image data of the mask images subjected to the image processing to the image memory 32 (step S9). Further, the image synthesizing circuit 33a may synthesize the image data of the mask images output from the image generating/processing circuit 31 together with the character information of various types of parameters, graduations, and the like and output the image data of the mask image to the display device 34a as a video signal and display it on the display device 34a, for example, on the fluoroscopic monitor 34aa.

On the completion of the mask imaging, the contrast medium is injected into the catheter in the body of the patient P from the injector 28 through the system controller 40. After the delay time set at step S7 passes from the start of injection of the contrast medium, the contrast imaging is automatically started by the rotation DSA. The operations of the high-voltage supply unit 26 and the drive device 27 are controlled through the system controller 40 and the X-ray is radiated from the X-ray tube 21 to the particular region of the patient P from many different directions while moving the C-arm 23 to a direction opposite to that in the mask imaging (the direction may be the same as that in the mask imaging.

The image generating/processing circuit 31 generates the image data of the contrast image of a frame unit based on the digitized projection data output from the X-ray detection unit 22 under the control of the CPU 35a and stores the image data to the image memory 32 as well as outputs it to the image synthesizing circuit 33a. The image generating/processing circuit 31 subjects the image data of the contrast images stored to the image memory 32 to the image processing when necessary under the control of the CPU 35a and stores the image data of the contrast images subjected to the image processing to the image memory 32 (step S10). Further, the image synthesizing circuit 33a synthesize the image data of the contrast images output from the image generating/processing circuit 31 together with the character information of various types of parameters, graduations, and the like and outputs the image data of the contrast images to the display device 34a as a video signal and displays the image data transmission apparatus of the contrast images on the display device 34a, for example, on the fluoroscopic monitor 34aa.

On the completion of the contrast imaging, the image data, which is used to reconstruct the 3D-DSA image, is generated based on the mask image and the contrast image by controlling the image generating/processing circuit 31 and the image memory 32 (step S11). Next, the image data generated at step S11 is transferred from the angio apparatus 6A to the 3D-WS7 through the network N.

When the CPU 35b of the 3D-WS7 executes the program, the image data of the 3D-DSA image is generated by subjecting the image data transferred from the angio apparatus 6A to a 3D reconstruction processing (step S12). The 3D-DSA image generated at step S12 is output to the image synthesizing circuit 33b.

The image synthesizing circuit 33b synthesizes the image data of the 3D-DSA image together with the character information of various types of parameters, graduations, and the like and outputs it to the display device 34b as a video signal. Accordingly, the image data of the 3D-DSA image of the particular region set at step S4 is displayed on the display device 34b (step S13).

According to the X-ray diagnostic system 1A of the embodiment, a 3D-DSA image having improved S/N and a small amount of artifact can be generated and displayed by optimizing the delay time for the 3D imaging while reducing unnecessary exposure of the patient P to the X-ray when the imaging is performed by the rotation DSA imaging execution unit 44. There is in particular a case that a fresh start of the imaging is performed because a manual skill depends on the technology of the examiner by the rotary DSA imaging, but, according to the X-ray diagnostic system 1A of the embodiment, unnecessary exposure of the patient P to the X-ray can be lost by the fresh start. More specifically, according to the X-ray diagnostic system 1A of the embodiment, the accuracy of the X-ray diagnosis can be improved while reducing the unnecessary exposure of the patient P to the X-ray.

Third Embodiment

Figure 9:
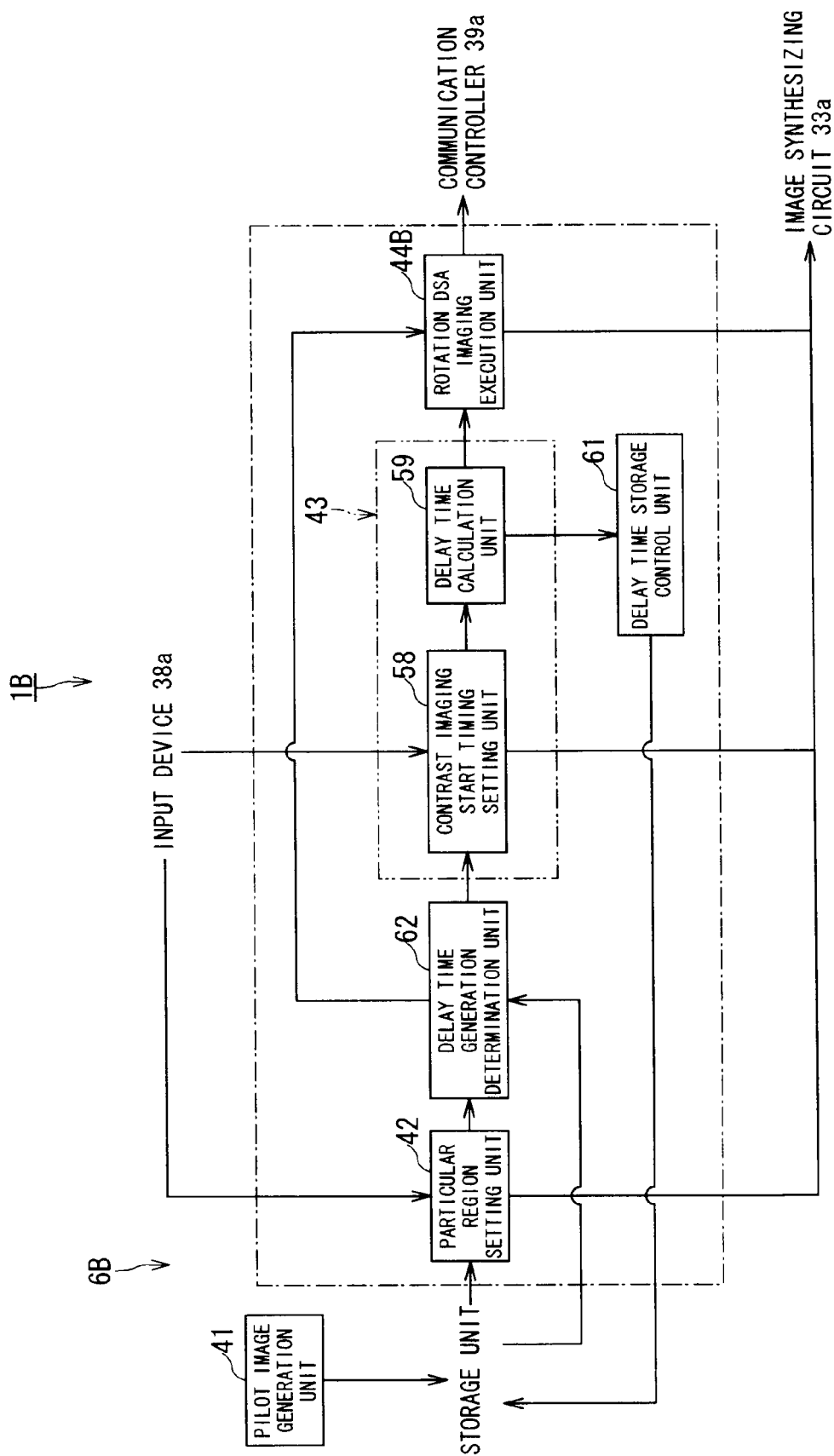
FIG. 9 is a block diagram showing a function of the third embodiment of the X-ray diagnostic system according to the present invention.

As shown in FIGS. 1, 5, and 9, an X-ray diagnostic system 1B of a third embodiment is composed of an angio apparatus 6B functioning as an X-ray diagnosis apparatus and a 3D-WS7. The X-ray diagnostic system 1B is different from the X-ray diagnostic system 1A of the second embodiment in that when the generating condition (generating condition: at least one an examiner such as an X-ray technologist, a doctor, and the like, a patient P, and a region) in the 3D imaging of a present examination accords with the generating condition stored in the 3D imaging in the past, the delay time employed in the past examination is employed in the present examination.

Since the hardware arrangement of the X-ray diagnostic system 1B of the third embodiment is the same as that of the X-ray diagnostic system 1 of first embodiment shown in FIG. 1, the explanation thereof is omitted. In contrast, the software arrangement of the X-ray diagnostic system 1B of the third embodiment will be explained below.

FIG. 9 is a block diagram showing a function of the third embodiment of the X-ray diagnostic system according to the present invention.

FIG. 9 shows a function of the angio apparatus 6B in the function of the X-ray diagnostic system 1B. Note that a function of the 3D-WS7 in the function of the X-ray diagnostic system 1B is the same as the function explained using FIG. 5, the explanation thereof is omitted.

As shown in FIG. 9, when a CPU 35a (shown in FIG. 1) executes a program, the angio apparatus 6B functions as a pilot image generation unit 41, a particular region setting unit 42, a delay time setting unit 43, a rotation DSA imaging execution unit 44B, a delay time storage control unit 61, and a delay time generation determination unit 62. Note that the pilot image generation unit 41 is not a component indispensable to the angio apparatus 6B. Although a case that the pilot image generation unit 41, the particular region setting unit 42, the delay time setting unit 43, the rotation DSA imaging execution unit 44B, the delay time storage control unit 61, and the delay time generation determination unit 62 are constructed by software is explained in the embodiment, the embodiment is not limited thereto, and they may be entirely or partly constructed by hardware composed of a circuit and the like.

The delay time storage control unit 61 has a function for storing the delay time calculated by a delay time calculation unit 59 of the delay time setting unit 43 to a storage unit such as an HD 37a (shown in FIG. 1) and the like together with the generating condition.

The delay time generation determination unit 62 has a function for determining whether or not the generating condition of the past examination, which accords with the generating condition of the present examination, is stored to the storage unit such as the HD 37a (shown in FIG. 1) and the like, and, when it is determined that the generating condition of the past examination, which accords with the generating condition of the present examination, is stored, supplying the delay time which corresponds to the generating condition of the past examination, which accords with the generating condition of the present examination, to the rotation DSA imaging execution unit 44B. In contrast, the delay time generation determination unit 62 has a function for causing the delay time setting unit 43 to generate the delay time as explained in the first embodiment when it is determined that no generating condition of the past examination, which accords with the generating condition of the present examination, is stored. When, for example, the examination condition is only the region, it is determined whether or not a region, which accords with a particular region of the present examination set by the particular region setting unit 42, is stored to the storage unit such as the HD 37*a* (shown in FIG. 1) and the like.

The rotation DSA imaging execution unit 44B has a function for calculating, when the delay time is supplied from the delay time generation determination unit 62, the image data of contrast images of the particular region employing the delay time supplied from the delay time generation determination unit 62 after mask imaging is finished and storing the image data to a storage unit such as an image memory 32 (shown in FIG. 1) and the like, in addition to a function similar to that of the rotation DSA imaging execution unit 44.

Note that the components of the angio apparatus 6B shown in FIG. 9, which are same as those of the angio apparatus 6A shown in FIG. 4, are denoted by the same reference numerals, and the explanation thereof is omitted.

Figure 10:
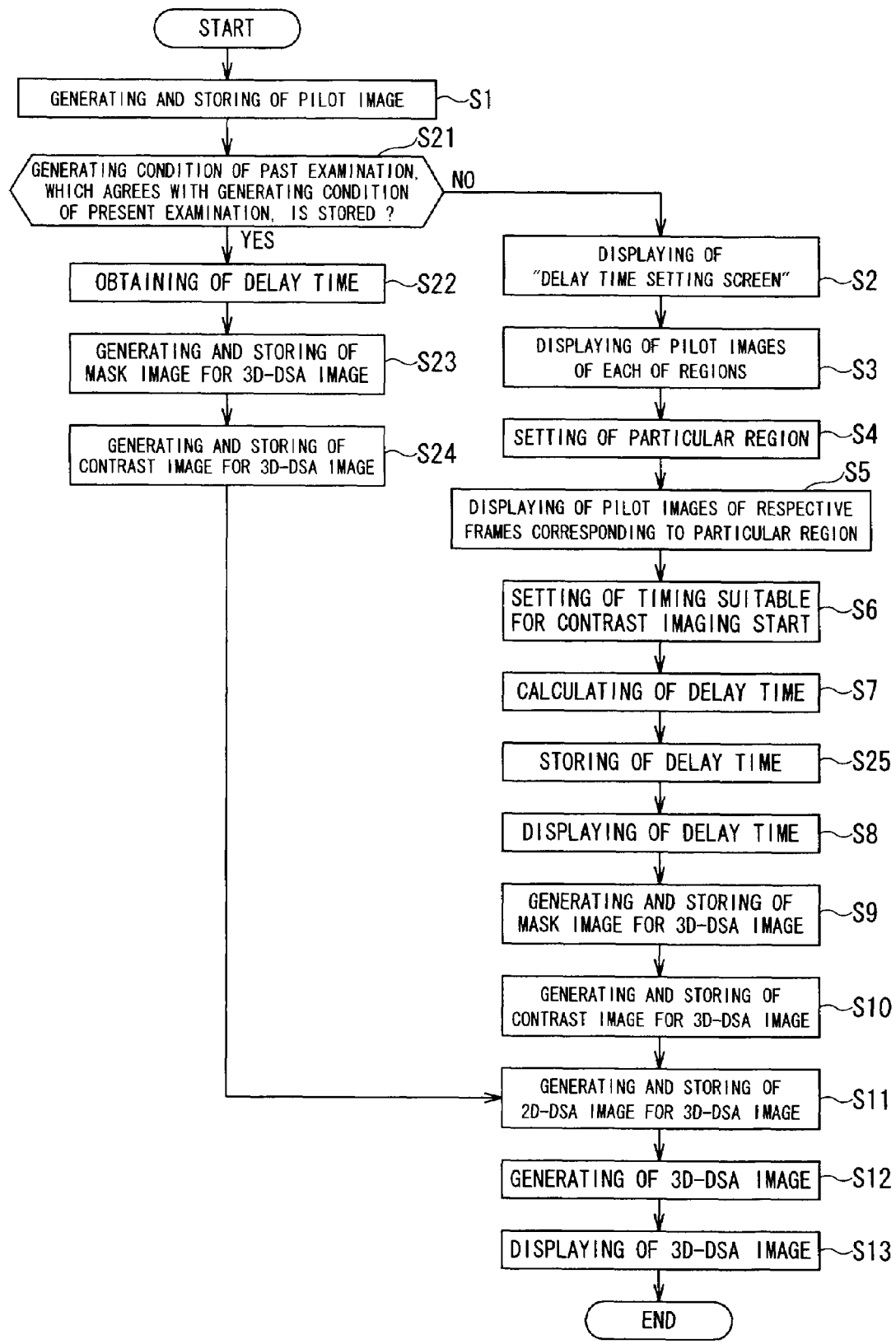
FIG. 10 is a flowchart showing an operation of the diagnostic system of the third embodiment.

Subsequently, an operation of the X-ray diagnostic system 1B of the embodiment will be explained using a flowchart shown in FIG. 10. Note that the steps of the flowchart shown in FIG. 10, which are same as those shown in FIG. 7, are denoted by the same reference numerals, and the explanation thereof is omitted.

First, a catheter is inserted into the body of the patient P placed on a table-top 25. When the CPU 35*a* of the angio apparatus 6B executes the program, the angio apparatus 6B performs the mask imaging by controlling a system controller 40, generates the image data of mask images of a plurality of regions, and causes the storage unit such as the image memory 32 and the like to store the image data.

Further, the angio apparatus 6B starts to automatically inject a contrast medium from an injector 28 by controlling the system controller 40. After the delay time set to a default value passes from the start of injection the contrast medium, the angio apparatus 6B automatically start contrast imaging. After the start of the contrast imaging, the angio apparatus 6B generates the image data of the contrast images of the region corresponding to the mask images and stores the image data to the storage unit such as the image memory 32 and the like.

Next, the image data of a 2D-DSA image as a pilot image is generated and stored based on the mask images and the contrast images by controlling an image generating/processing circuit 31, the image memory 32 and the HD 37*a* (step S1). Since mask images and contrast images are generated to the plurality of regions, pilot images are generated to the plurality of regions.

Next, it is determined whether or not the generating condition of the past examination, which accords with the generating condition of the present examination, is stored to the storage unit such as the HD 37*a* and the like (step S21). When the determination at step S21 is YES, that is, when it is determined that the generating condition of the past examination, which accords with the generating condition of the present examination, is stored, the delay time corresponding to the generating condition of the past examination which accords with the generating condition of the present examination is obtained from the storage unit (step S22). Next, the 3D imaging is started.

In the 3D imaging, first, the mask imaging is started by rotation DSA. In the mask imaging, the operations of a high-voltage supply unit 26 and a drive device 27 are controlled through the system controller 40, and an X-ray is radiated from an X-ray tube 21 to the particular region of the patient P from many different directions while moving a C-arm 23 and a table-top 25 to a position suitable for the mask imaging.

The image generating/processing circuit 31 generates the image data of the mask image of a frame unit based on the digitized projection data output from an X-ray detection unit 22 under the control of the CPU 35*a* and stores the image data to the image memory 32 as well as outputs it to an image synthesizing circuit 33*a*. The image generating/processing circuit 31 subjects the image data of the mask images stored to the image memory 32 to an image processing when necessary under the control of the CPU 35*a* and stores the image data of the mask images subjected to the image processing to the image memory 32 (step S23).

On the completion of the mask imaging, the contrast medium is injected into the catheter in the body of the patient P from the injector 28 through the system controller 40. After the delay time obtained at step S22 passes from the start of injection of the contrast medium, the contrast imaging is automatically started by the rotation DSA. The operations of the high-voltage supply unit 26 and the drive device 27 are controlled through the system controller 40, and the X-ray is radiated from the X-ray tube 21 to the particular region of the patient P from many different directions while moving the C-arm 23 to a direction opposite to that in the mask imaging (the direction may be the same as that in the mask imaging).

The image generating/processing circuit 31 generates the image data of the contrast image of the frame unit based on the digitized projection data output from the X-ray detection unit 22 under the control of the CPU 35*a* and stores the image data to the image memory 32 as well as outputs it to the image synthesizing circuit 33*a*. The image generating/processing circuit 31 subjects the image data of the contrast images stored to the image memory 32 to an image processing when necessary under the control of the CPU 35*a* and stores the image data of the contrast images subjected to the image processing to the image memory 32 (step S24). Further, the image synthesizing circuit 33*a* synthesizes the image data of the contrast images stored to the image memory 32 together with the character information of various types of parameters, graduations, and the like and outputs the image data of the contrast images to the display device 34*a* as a video signal and displays it on the display device 34*a*, for example, on the fluoroscopic monitor 34*aa*.

On the completion of the contrast imaging, the image data, which is used to reconstruct a 3D-DSA image, is generated based on the mask images and the contrast images by controlling the image generating/processing circuit 31 and the image memory 32 (step S11).

In contrast, when the determination at step S21 is NO, that is, it is determined that no generating condition of the past examination, which accords with the generating condition of the present examination, is stored, a "delay time setting screen" is displayed (step S2).

Further, the delay time calculated at step S7 is stored to the storage unit such as the HD 37*a* (shown in FIG. 1) and the like together with the generating condition (step S25).

According to the X-ray diagnostic system 1B of the embodiment, a 3D-DSA image having improved S/N and a small amount of artifact can be generated and displayed by optimizing the delay time for the 3D imaging while reducing unnecessary exposure of the patient P to the X-ray when the imaging is performed by the rotation DSA imaging execution unit 44B. There is in particular a case that a fresh start of the imaging is performed because a manual skill depends on the technology of the examiner by the rotary DSA imaging, but, according to the X-ray diagnostic system 1B of the embodiment, unnecessary exposure of the patient P to the X-ray can be lost by the fresh start. More specifically, according to the X-ray diagnostic system 1B of the embodiment, the accuracy of the X-ray diagnosis can be improved while reducing the unnecessary exposure of the patient P to the X-ray.

Fourth Embodiment

Figure 11:
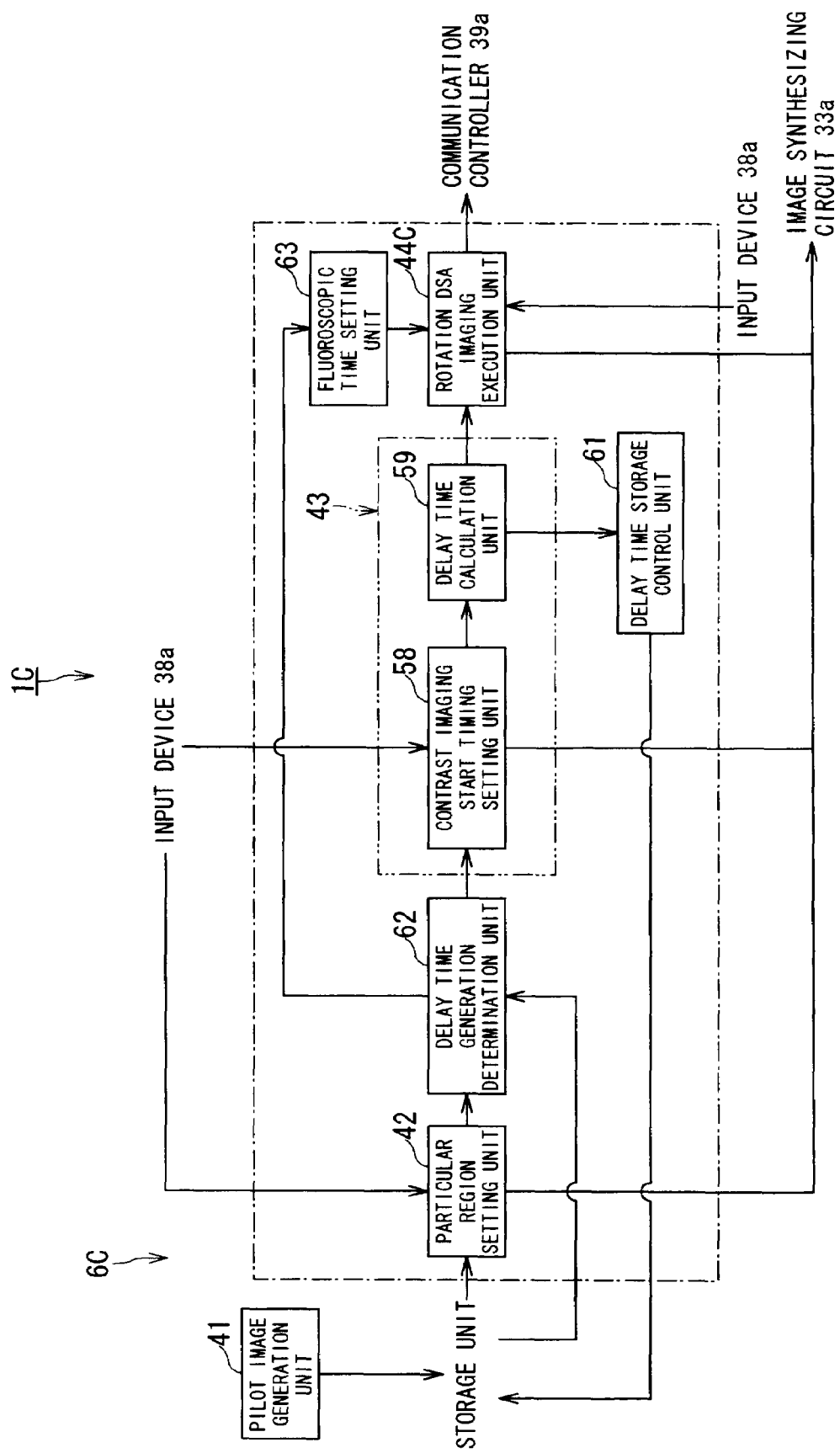
FIG. 11 is a block diagram showing a function of the fourth embodiment of the X-ray diagnostic system according to the present invention.

As shown in FIGS. 1, 5, and 11, an X-ray diagnostic system 1C of a fourth embodiment is composed of an angio apparatus 6C functioning as an X-ray diagnosis apparatus and a 3D-WS7. The X-ray diagnostic system 1C shows a modification of the X-ray diagnostic system 1B of the third embodiment.

Since the hardware arrangement of the X-ray diagnostic system 1C of the fourth embodiment is the same as that of the X-ray diagnostic system 1 of the first embodiment shown in FIG. 1, the explanation thereof is omitted. In contrast, the software arrangement of the X-ray diagnostic system 1C of the fourth embodiment will be explained below.

FIG. 11 is a block diagram showing a function of the fourth embodiment of the X-ray diagnostic system according to the present invention.

FIG. 11 shows a function of the angio apparatus 6C in the function of the X-ray diagnostic system 1C. Note that since a function of the 3D-WS7 in the function of the X-ray diagnostic system 1C is the same as the function explained using FIG. 5, the explanation thereof is omitted.

As shown in FIG. 11, when a CPU 35a (shown in FIG. 1) executes a program, the angio apparatus 6C functions as a pilot image generation unit 41, a particular region setting unit 42, a delay time setting unit 43, a rotation DSA imaging execution unit 44C, a delay time storage control unit 61, a delay time generation determination unit 62, and a fluoroscopic time setting unit 63. Note that the pilot image generation unit 41 is not a component indispensable to the angio apparatus 6C. Further, although a case that the pilot image generation unit 41, the particular region setting unit 42, the delay time setting unit 43, the rotation DSA imaging execution unit 44C, the delay time storage control unit 61, the delay time generation determination unit 62, and the fluoroscopic time setting unit 63 are constructed by software is explained in the embodiment, the embodiment is not limited thereto, and they may be entirely or partly constructed by hardware composed of a circuit and the like.

The fluoroscopic time setting unit 63 has such a function that, when the delay time generation determination unit 62 determines that the generating condition of a past examination, which accords with the generate condition of a present examination, is stored, the fluoroscopic time setting unit 63 generates a fluoroscopic time which is shorter than the delay time corresponding to the generating condition of the past examination which accords with the generate condition of the present examination. The fluoroscopic time is determined by subtracting a time previously set to each region, for example, two or three seconds from the delay time output from the delay time generation determination unit 62.

The rotation DSA imaging execution unit 44C has a function for performing a fluoroscopy and displaying a fluoroscopic image on the display device 34a, for example, the fluoroscopic monitor 34aa through an image synthesizing circuit 33a during the fluoroscopic time, which is generated by and supplied from the fluoroscopic time setting unit 63 from the start of injection of a contrast medium until a contrast imaging start signal is input from an input device 38a in addition to the function of the rotation DSA imaging execution unit 44 (shown in FIG. 4). The rotation DSA imaging execution unit 44C has such a function that when the contrast imaging start signal is input from the input device 38a, it finishes the fluoroscopy, starts contrast imaging, calculates the image data of a contrast image, and stores the image data to a storage unit such as an image memory 32 (shown in FIG. 1), and the like.

Note that the components of the angio apparatus 6C shown in FIG. 11, which are the same as those of the angio apparatus 6A shown in FIG. 4, are denoted by the same reference numerals, and the explanation thereof is omitted.

Figure 12:
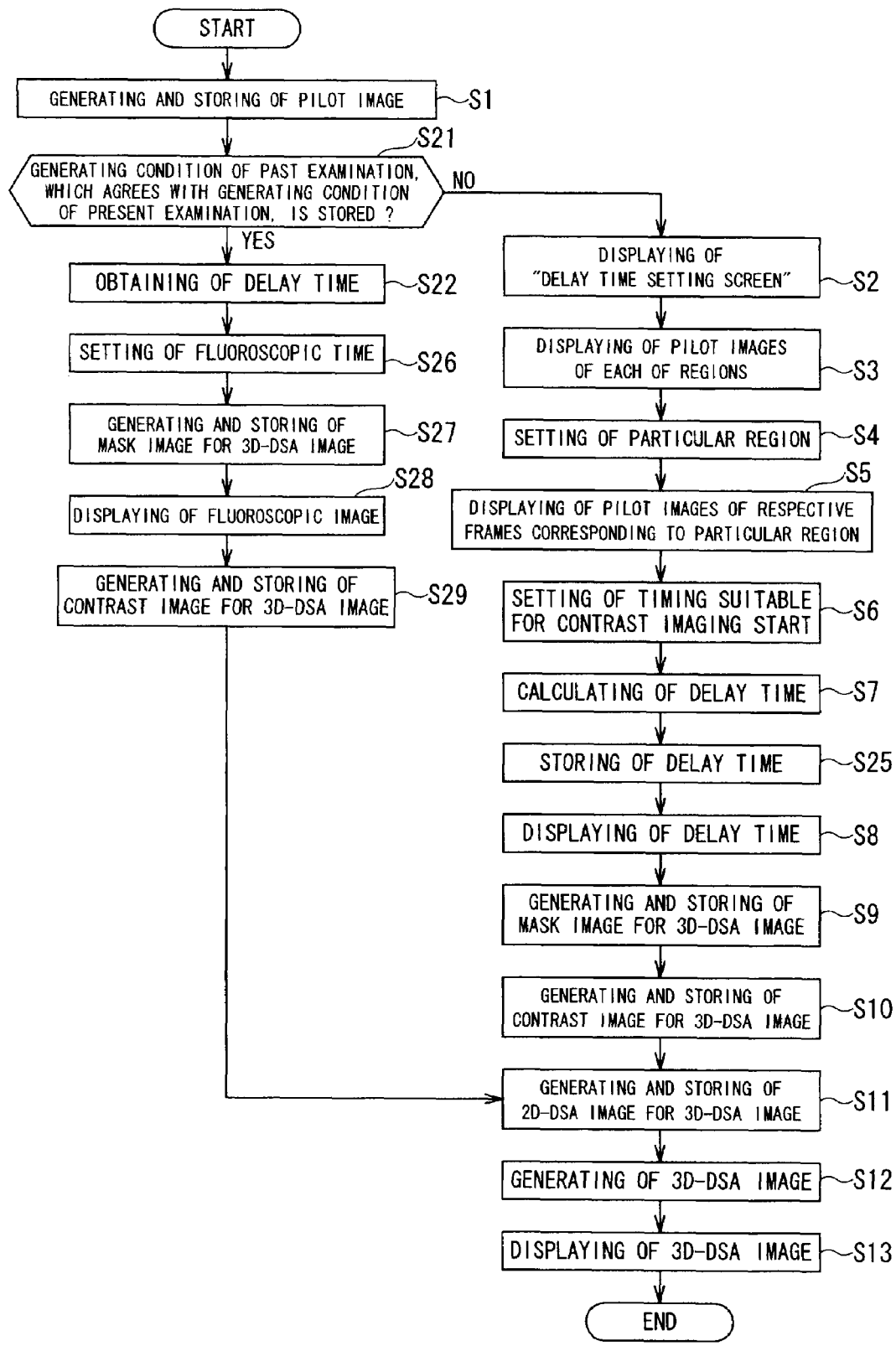
FIG. 12 is a flowchart showing an operation of the diagnostic system of the fourth embodiment.

Subsequently, an operation of the X-ray diagnostic system 1C of the embodiment will be explained using a flowchart shown in FIG. 12. Note that the steps of the flowchart shown in FIG. 12, which are same as those of a flowchart shown in FIG. 10, are denoted by the same reference numerals, and the explanation thereof is omitted.

A fluoroscopic time is set based on the delay time obtained by step S22 (step S26). The fluoroscopic time is determined by subtracting the time previously set to each region from the delay time obtained at step S22. Next, 3D imaging is started.

In the 3D imaging, first, mask imaging is started by rotation DSA. In the mask imaging, the operations of a high-voltage supply unit 26 and a drive device 27 are controlled through a system controller 40 and an X-ray is radiated from an X-ray tube 21 to a particular region of a patient P from many different directions while moving a C-arm 23 and a table-top 25 to a position suitable for the mask imaging.

An image generating/processing circuit 31 generates the image data of the mask image of a frame unit based on the digitized projection data output from an X-ray detection unit 22 under the control of a CPU 35a and stores the image data to an image memory 32 as well as outputs it to an image synthesizing circuit 33a. The image generating/processing circuit 31 subjects the image data of the mask images stored to the image memory 32 to an image processing when necessary under the control of the CPU 35a and stores the image data of the mask images subjected to the image processing to the image memory 32 (step S27). Further, the image synthesizing circuit 33a synthesizes the image data of the mask images output from the image generating/processing circuit 31 together with the character information of various types of parameters, graduations, and the like, outputs the image data of the mask images to a display device 34a as a video signal, and displays it on the display device 34a, for example, on the fluoroscopic monitor 34aa.

On the completion of the mask imaging, the contrast medium is injected into a catheter in the body of the patient P from an injector 28 through the system controller 40. The fluoroscopy is automatically performed during the fluoroscopic time set at step S26 from the start of injection of the contrast medium, and a fluoroscopy image is displayed on the display device 34a, for example, on the fluoroscopic monitor 34aa (step S28).

An examiner inputs a "contrast imaging start" using the input device 38a while observing the fluoroscopy image displayed at step S28. When the input device 38a instructs to start the contrast imaging, the contrast imaging is started by the rotation DSA from the timing of input of the instruction. The operations of the high-voltage supply unit 26 and the drive device 27 are controlled through the system controller 40 and the X-ray is radiated from the X-ray tube to the particular region of the patient P in many different directions while moving the C-arm 23 to a direction opposite to that in the mask imaging (the direction may be the same as that in the mask imaging).

The image generating/processing circuit 31 generates the image data of the mask image of the frame unit based on the digitized projection data output from the X-ray detection unit 22 under the control of the CPU 35*a* and stores the image data to the image memory 32 as well as outputs it to the image synthesizing circuit 33*a*. The image generating/processing circuit 31 subjects the image data of the mask images stored to the image memory 32 to an image processing when necessary under the control of the CPU 35*a* and stores the image data of the contrast images subjected to the image processing to the image memory 32 (step S29). Further, the image synthesizing circuit 33*a* synthesizes the image data of the contrast images stored to the image memory 32 together with the character information of various types of parameters, graduations, and the like, outputs the image data of the contrast images to the display device 34*a* as a video signal, and displays it on the display device 34*a*, for example, on the fluoroscopic monitor 34*aa*.

On the completion of the contrast imaging, the image data, which is used to reconstruct a 3D-DSA image, is generated based on the mask images and the contrast images by controlling the image generating/processing circuit 31 and the image memory 32 (step S11).

According to the X-ray diagnostic system 1C of the embodiment, a 3D-DSA image having improved S/N and a small amount of artifact can be generated and displayed by optimizing the delay time for the 3D imaging while reducing unnecessary exposure of the patient P to the X-ray when the imaging is performed by the rotation DSA imaging execution unit 44C. There is in particular a case that a fresh start of the imaging is performed because a manual skill depends on the technology of the examiner by the rotary DSA imaging, but, according to the X-ray diagnostic system 1C of the embodiment, unnecessary exposure of the patient P to the X-ray can be lost by the fresh start. Further, according to the X-ray diagnostic system 1C of the embodiment, unnecessary exposure of the patient P to the X-ray can be reduced by reducing the fluoroscopic time to the contrast imaging start. More specifically, according to the X-ray diagnostic system 1C of the embodiment, the accuracy of the X-ray diagnosis can be improved while reducing the unnecessary exposure of the patient P to the X-ray.

Fifth Embodiment

Figure 13:
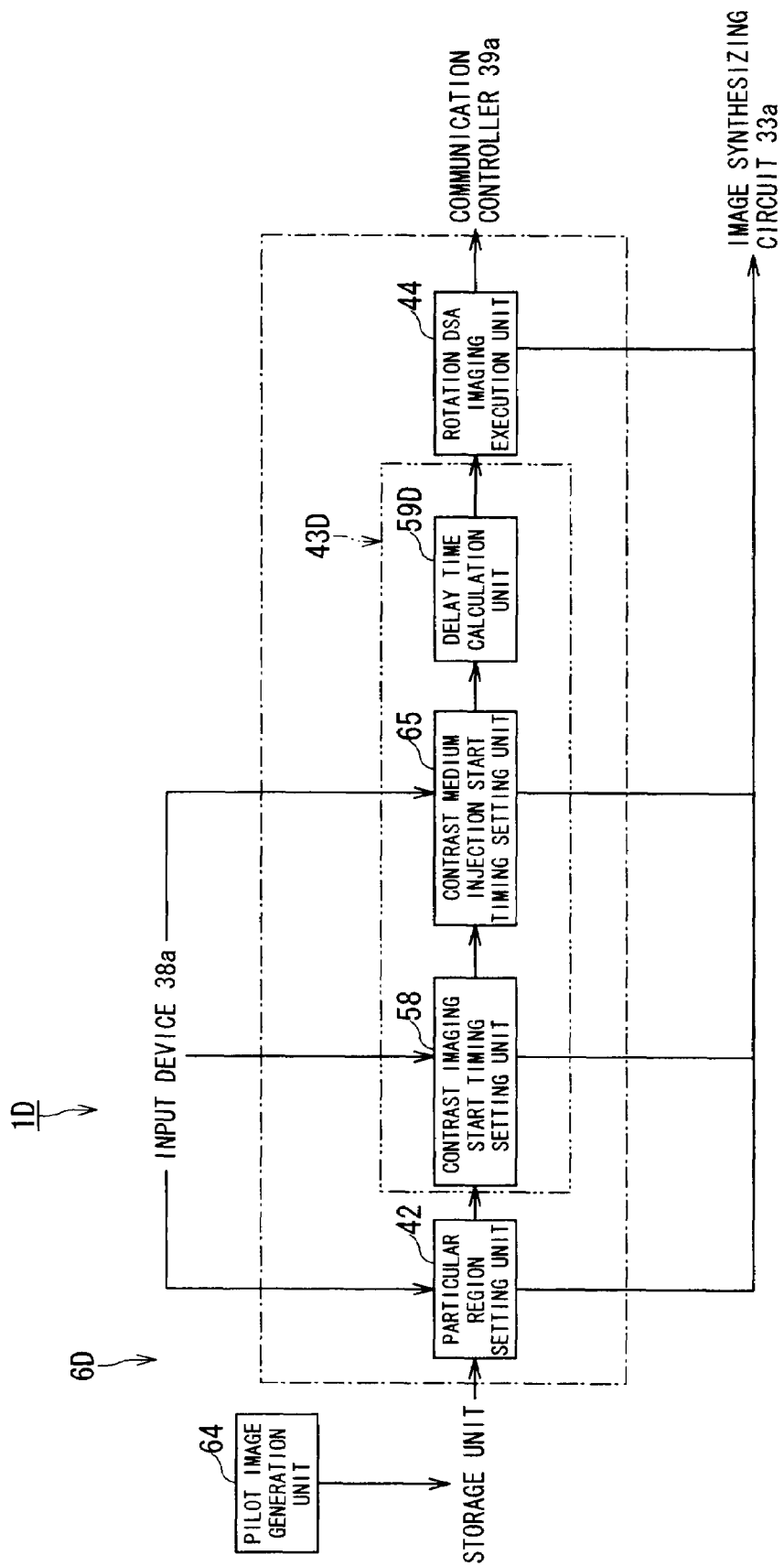
FIG. 13 is a block diagram showing a function of the fifth embodiment of the X-ray diagnostic system according to the present invention.

As shown in FIGS. 1, 5, and 13, a diagnostic system 1D of a fifth embodiment is composed of an angio apparatus 6D functioning as an X-ray diagnosis apparatus and a 3D-WS7. The X-ray diagnostic system 1D is different from the X-ray diagnostic system 1C of the fourth embodiment in that an examiner manually injects a contrast medium when a pilot image is generated prior to 3D imaging. When the examiner manually injects the contrast medium, a correct timing at which the contrast medium is injected is not apparent.

Since the hardware arrangement of the X-ray diagnostic system 1D of the fifth embodiment is the same as that of the X-ray diagnostic system 1 of the first embodiment shown in FIG. 1, the explanation thereof is omitted. In contrast, the software arrangement of the X-ray diagnostic system 1D of the fourth embodiment will be explained below.

FIG. 13 is a block diagram showing a function of the fifth embodiment of the X-ray diagnostic system according to the present invention.

FIG. 13 shows a function of the angio apparatus 6D in the function of the X-ray diagnostic system 1D. Note that since a function of the 3D-WS7 in the function of the X-ray diagnostic system 1D is the same as the function explained using FIG. 5, the explanation thereof is omitted.

As shown in FIG. 13, when a CPU 35*a* (shown in FIG. 1) executes a program, the angio apparatus 6D functions as a pilot image generation unit 64, a particular region setting unit 42, a delay time setting unit 43D, and a rotation DSA imaging execution unit 44 in a series of examinations. Further, the delay time setting unit 43D includes a contrast imaging start timing setting unit 58, a contrast medium injection start timing setting unit 65, and a delay time calculation unit 59D. Note that although a case that the pilot image generation unit 64, the particular region setting unit 42, the delay time setting unit 43D, and the rotation DSA imaging execution unit 44 are constructed by software is explained in the embodiment, the embodiment is not limited thereto, and they may be entirely or partly constructed by hardware composed of a circuit and the like.

The pilot image generation unit 64 has a function for generating the image data of the pilot image which generates a delay time employed when the 3D imaging is performed to a particular region of a patient P.

Specifically, the pilot image generation unit 64 performs mask imaging by controlling a system controller 40 (shown in FIG. 1), generates the image data of mask images of respective regions of the patient P, and stores the image data to a storage unit such as an image memory 32 (shown in FIG. 1) and the like. Further, the pilot image generation unit 64 performs contrast imaging to the regions corresponding to the mask images after it starts the contrast imaging by controlling the system controller 40, generates the image data contrast images of the respective regions of the patient P, and stores the image data to the storage unit such as the image memory 32 (shown in FIG. 1) and the like. Note that after the contrast imaging is started, the examiner manually injects the contrast medium at an arbitrary timing.

Further, the pilot image generation unit 64 generates the image data of a pilot image as a 2D blood vessel image by a subtraction processing based on the mask images and the contrast images by controlling an image generating/processing circuit 31 and the image memory 32 (both of them shown in FIG. 1). Note that pilot image is stored to the storage unit such as the image memory 32 (shown in FIG. 1) and the like. When the pilot image generation unit 64 generates pilot images of a plurality of regions of the patient P, the pilot image of each of the plurality of regions is stored to the storage unit.

The contrast medium injection start timing setting device 65 has a function for setting a contrast medium injection start timing, which is suitable to start injection of the contrast medium to perform the 3D imaging to the particular region, based on a particular frame, which is selected from the pilot images of respective frames corresponding to the particular region displayed on a reference monitor 34*ab* by the contrast imaging start timing setting unit 58, and a frame rate employed when the pilot image of the particular region is generated. Specifically, the contrast medium injection start timing setting device 65 sets the contrast medium injection start timing $(n_a/R)$ based on the pilot image of an $n_a$-th $(n_a<n_s, n_a=1, 2, 3, \ldots)$ frame selected from the pilot images of the respective frames corresponding to the particular region and the frame rate R employed when the pilot image of the particular region is generated.

The delay time calculation device 59D has a function for calculating the delay time $T_2$, which employed when the 3D imaging is performed to the particular region, based on the contrast medium injection start timing $(n_s/R)$ set by the contrast imaging start timing setting unit 58 and the contrast medium injection start timing $(n_d/R)$ set by the contrast medium injection start timing setting device 65. For example, the delay time calculation device 59D calculates the delay time T, which is employed when the 3D imaging is performed to the particular region, using a following equation (2).

$$T_2 = (n_s - n_a)/R \tag{2}$$

Figure 14:
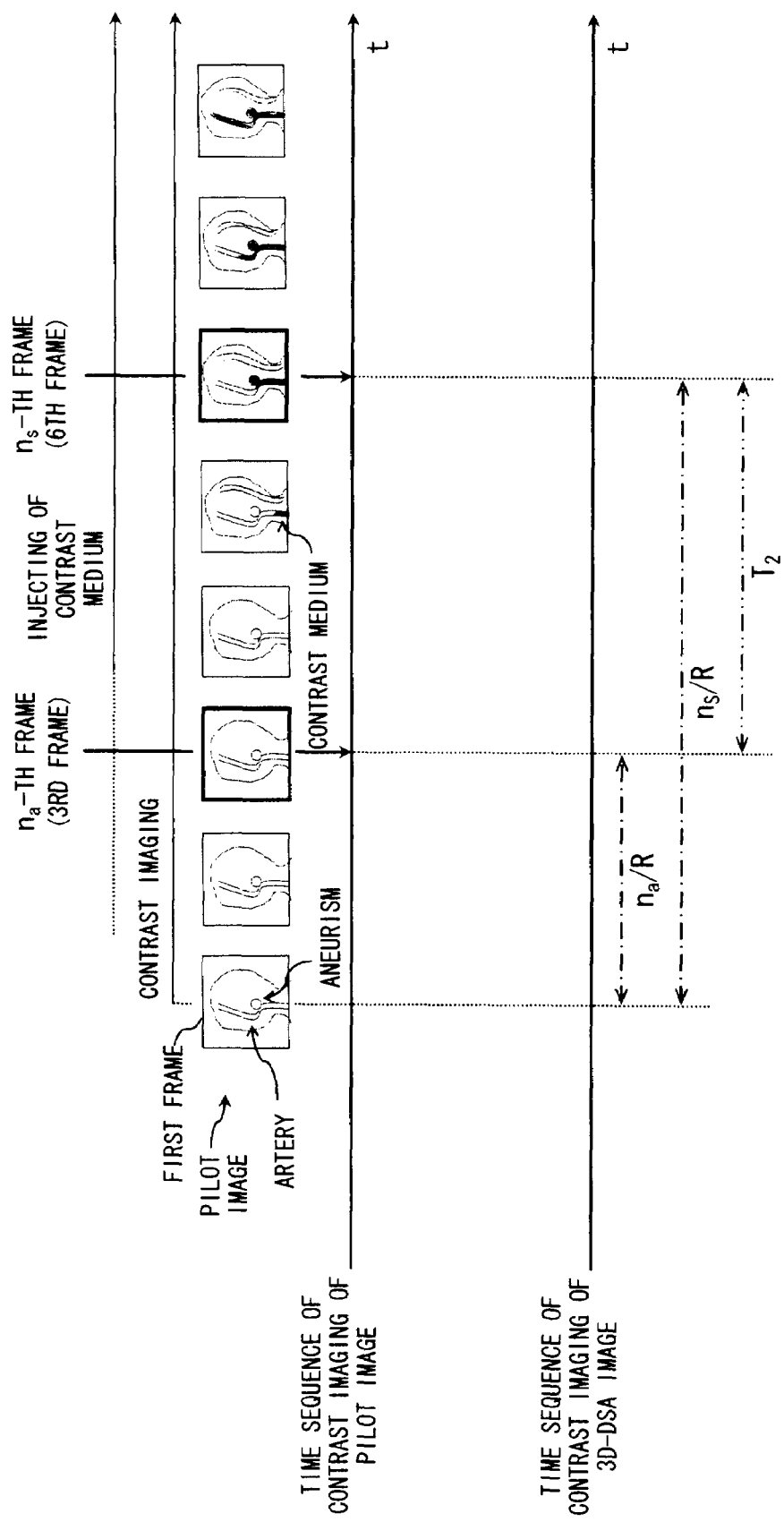
FIG. 14 is a view explaining an equation (2) for calculating a delay time employed when a 3D imaging of a particular region is performed.

FIG. 14 is a view explaining the equation (2) for calculating the delay time $T_2$ employed when the 3D imaging is performed to the particular region.

An upper part of FIG. 14 shows a time-sequence (t) of the contrast imaging of the pilot images performed to the particular region by the pilot image generation unit 41 and the pilot images. In the contrast imaging of the pilot images, first, the contrast imaging is started at a certain timing, and the contrast medium starts to be manually injected at an unknown timing in the midway of the contrast imaging.

A lower part of FIG. 14 shows a time-sequence (t) designed based on the upper part and shows the time-sequence (t) of the contrast imaging included in the 3D imaging performed to the particular region. The delay time $T_2$, which is employed when the contrast imaging is performed, is calculated by the equation (2) based on the $n_a$-th frame, the $n_s$-th frame, and the frame rate R applied to the image data.

Note that the components of the angio apparatus 6D shown in FIG. 13, which are the same as those of the angio apparatus 6A shown in FIG. 4, are denoted by the same reference numerals, and the explanation thereof is omitted.

Figure 15:
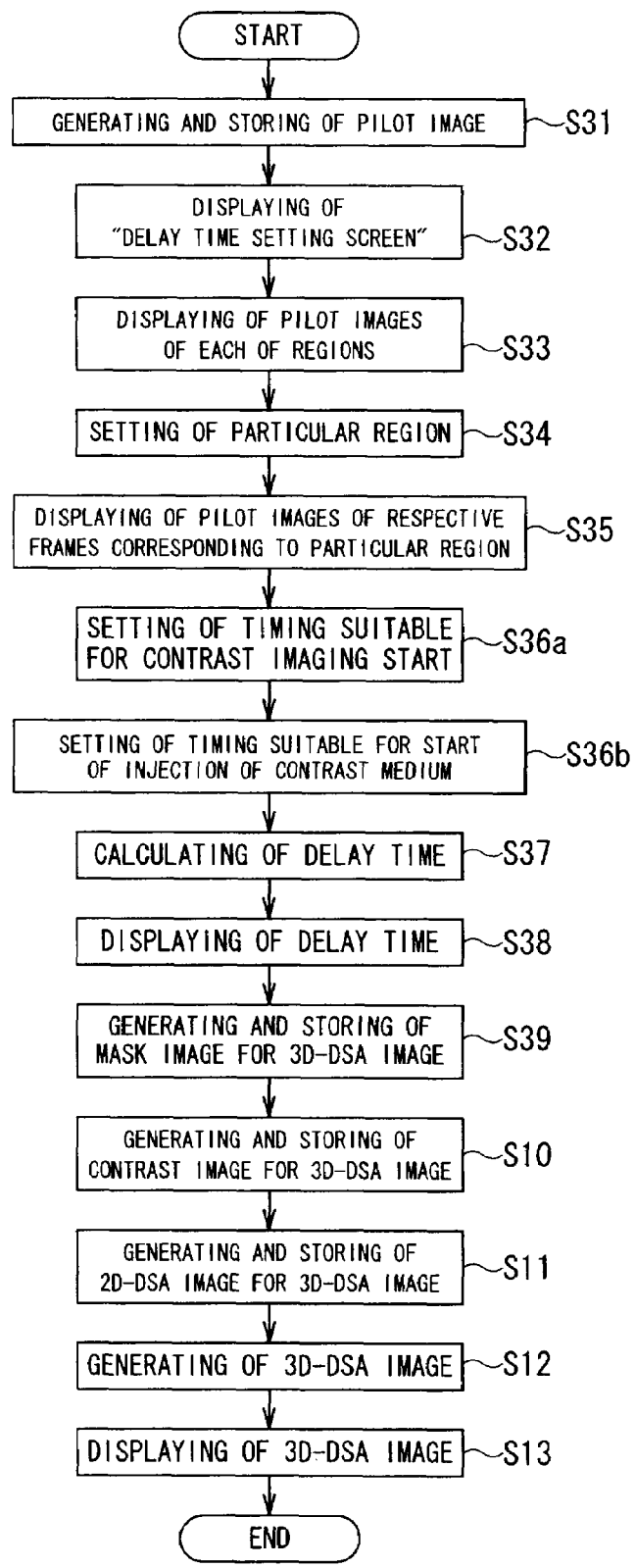
FIG. 15 is a flowchart showing an operation of the diagnostic system of the fifth embodiment.

Subsequently, an operation of the X-ray diagnostic system 1D of the embodiment will be explained using a flowchart shown in FIG. 15. Note that steps of the flowchart shown in FIG. 15, which are same as those of the flowchart shown in FIG. 7, are denoted by the same reference numerals, and the explanation thereof is omitted.

First, a catheter is inserted into the body of the patient P placed on a table-top 25. When the CPU 35a of the angio apparatus 6D executes the program, the angio apparatus 6D performs the mask imaging by controlling the system controller 40, generates the image data of the mask images from one direction of the plurality of regions, and stores the image data to the storage unit such as the image memory 32 (shown in FIG. 1) and the like.

Further, the angio apparatus 6D starts the contrast imaging by controlling the system controller 40. After an arbitrary time passes from the start of the contrast imaging, the examiner starts to manually inject the contrast medium. After the start of the contrast imaging, the image data of the contrast image from one direction of the region corresponding to the mask image is generated and stored to the storage unit such as the image memory 32 and the like.

Next, the image data of a 2D-DSA image, which is a pilot image as a 2D angiogram, is generated and stored based on the mask image and the contrast image from one direction by controlling the image generating/processing circuit 31, the image memory 32 and the HD 37a (step S31). When mask images and contrast images are generated to the plurality of regions, a pilot image is generated and stored to each of the plurality of regions at step S31.

Next, when a 3D-DSA imaging program is selected, a "delay time setting screen" is displayed on a display device 34a, for example, on a system monitor 34ac (step S32, screen of left edge in FIG. 8). The delay time set to a default value is displayed on the "delay time setting screen".

When the examiner clicks a "confirm" button on the "delay time setting screen", the pilot image of each region which is generated and stored at step S31 is read out and displayed on the display device 34a, for example, on the reference monitor 34ab as a thumbnail image (step S33, second screen from left in FIG. 8). Further, the particular region to which the 3D imaging is performed is set based on the pilot images of the respective regions displayed on the reference monitor 34ab (step S34). Specifically, a region C2 is set as the particular region by the examiner who selects the region C2 from the respective regions (region C1, C2, C3, . . . ) displayed on the reference monitor 34ab using an input device 38a.

Next, the pilot images of the respective frames corresponding to the particular region set at step S34 are time-sequentially displayed on the display device 34a, for example, on the reference monitor 34ab as thumbnail images (step S35, second screen from right in FIG. 8). Further, the pilot image of the $n_s$-th frame corresponding to the start of the contrast imaging is selected based on the pilot images of the respective frames (first frame, second frame, third frame, . . . ) corresponding to the particular region displayed on the reference monitor 34ab. Specifically, the examiner selects the pilot image C2-6 of the $n_s$-th frame, for example, a sixth frame from the pilot images of the respective frames corresponding to the region C as the particular region. Note that the examiner preferably selects a frame in which the contrast medium reaches an interest region (for example, a region where aneurism exists) when a 3D-DSA image is generated.

Further, the contrast imaging start timing, at which the contrast imaging is suitably started, is set based on the selected $n_s$-th frame and the frame rate employed when the pilot image of the particular region is generated (step S36a).

Next, the $n_a$-th frame, which corresponds to the start of injection of the contrast medium, is selected based on the pilot images of the respective frames corresponding to the particular region displayed on the reference monitor 34ab at step S35. Specifically, the examiner selects the pilot image C2-3 of the $n_a$-th frame, for example, a third frame from the pilot images of the respective frames corresponding to the region C using the input device 38a.

Further, the contrast medium injection start timing, which is suitable for the start of injection of the contrast medium is set based on the selected $n_a$-th frame and the frame rate employed when the pilot image of the particular region is generated (step S36b).

Next, the delay time, which is employed when the 3D imaging of the particular region is performed, is calculated using the equation (2) based on the contrast imaging start timing set at step S36a and the contrast medium injection start timing set at step S36b (step S37).

The delay time calculated at step S37 is displayed on the display device 34a, for example, on the system monitor 34a (step S8, screen of right edge in FIG. 8). When the examiner pushes an imaging-start switch after a completion of preparations for the 3D imaging, the 3D imaging is started.

According to the X-ray diagnostic system 1D of the embodiment, a 3D-DSA image having improved S/N and a small amount of artifact can be generated and displayed by optimizing the delay time for the 3D imaging while reducing unnecessary exposure of the patient P to the X-ray when the imaging is performed by the rotation DSA imaging execution unit 44. There is in particular a case that a fresh start of the imaging is performed because a manual skill depends on the technology of the examiner by the rotary DSA imaging, but, according to the X-ray diagnostic system 1D of the embodiment, unnecessary exposure of the patient P to the X-ray can be lost by the fresh start. More specifically, according to the X-ray diagnostic system 1D of the embodiment, the accuracy of the X-ray diagnosis can be improved while reducing the unnecessary exposure of the patient P to the X-ray.

Sixth Embodiment

Figure 16:
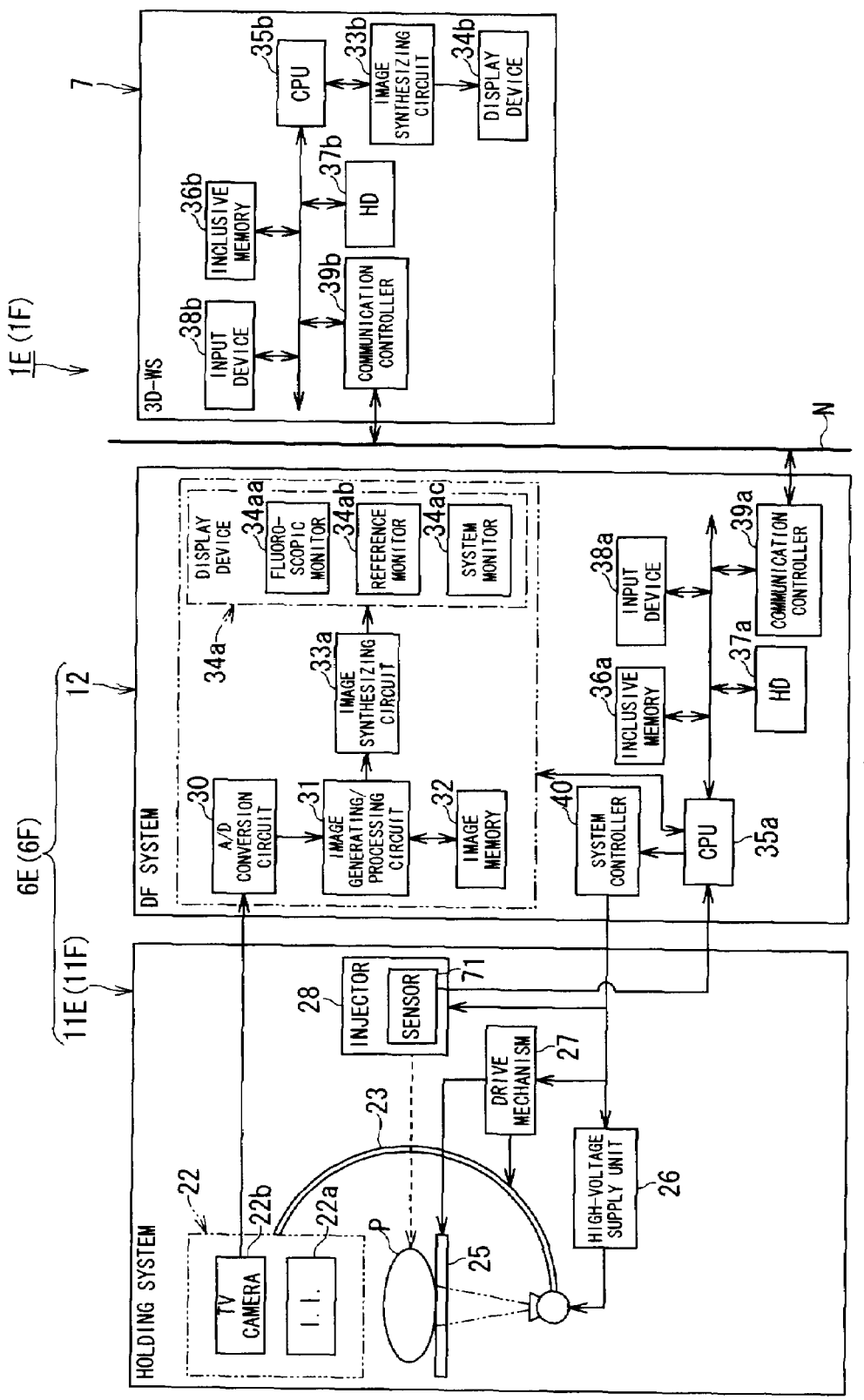
FIG. 16 is a schematic view showing a hardware arrangement of sixth-seventh embodiments of the X-ray diagnostic system according to the present invention.
Figure 17:
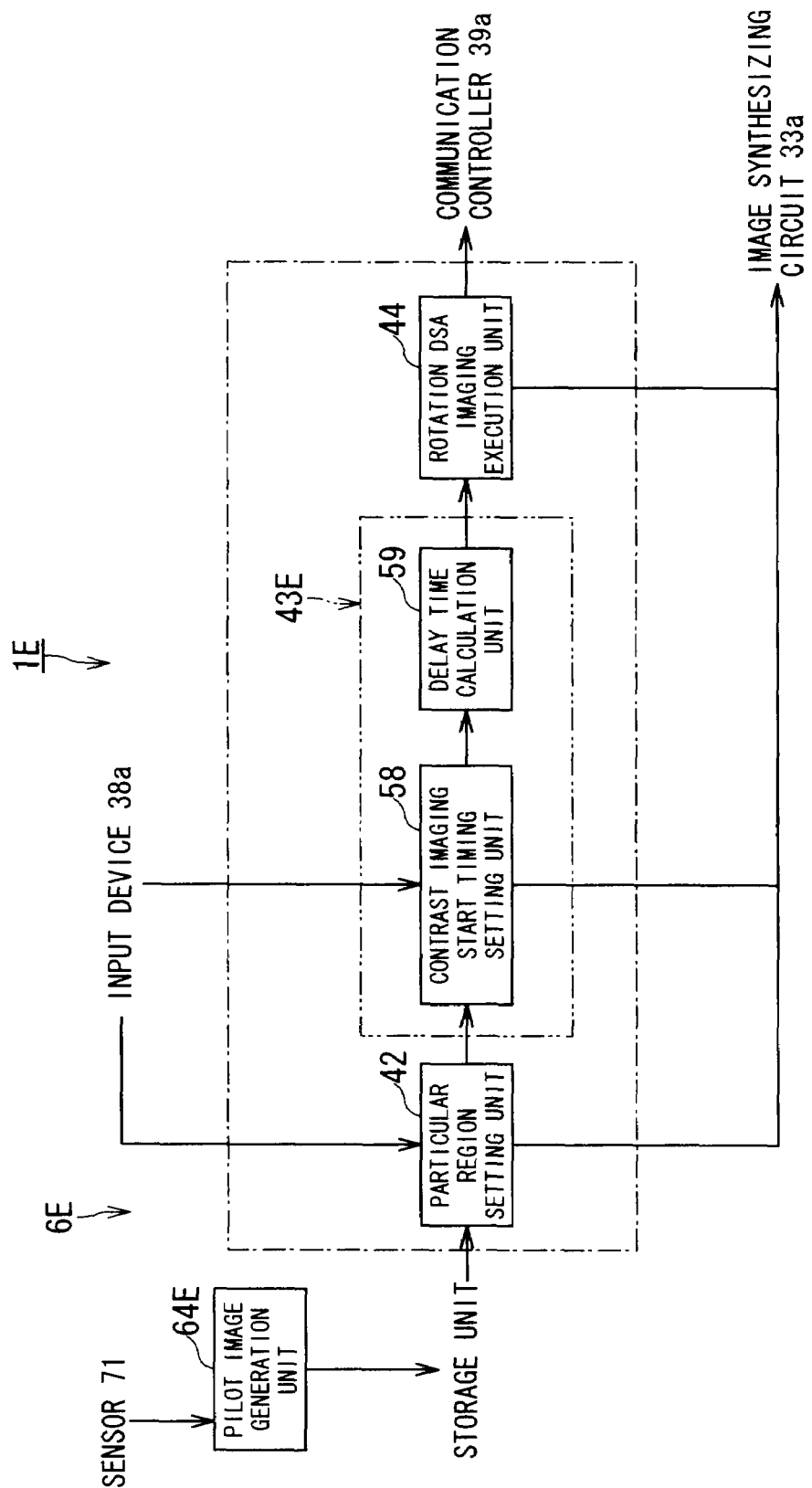
FIG. 17 is a block diagram showing a function of the sixth embodiment of the X-ray diagnostic system according to the present invention.

As shown in FIGS. 5, 16 and 17, an X-ray diagnostic system 1E of a sixth embodiment is composed of an angio apparatus 6E functioning as an X-ray diagnosis apparatus and a 3D-WS7. The X-ray diagnostic system 1E is common to the X-ray diagnostic system 1D of the fifth embodiment in that an examiner manually injects a contrast medium when a pilot image is generated prior 3D imaging. Further, the contrast medium injection start timing setting device 65, which is disposed to the angio apparatus 6D constituting the X-ray diagnostic system 1D of the fifth embodiment, sets an $n_a$-th frame as a frame suitable for the start of injection of the contrast medium by selecting the pilot image of the $n_a$-th frame from the pilot images of the respective frames corresponding to a particular region. However, it may be difficult to select the $n_a$-th frame. The diagnostic system 1E is different from the X-ray diagnostic system 1D of the fifth embodiment in that the diagnostic system 1E make it unnecessary for the examiner to select the $n_a$-th frame by actually measuring a contrast medium injection timing.

FIG. 16 is a schematic view showing a hardware arrangement of the sixth embodiment of the X-ray diagnostic system according to the present invention.

FIG. 16 shows the X-ray the diagnostic system 1E of the embodiment. The X-ray the diagnostic system 1E is composed of the angio apparatus 6E functioning as the X-ray diagnosis apparatus and the 3D-WS7 connected to the angio apparatus 6E through a network N so that the angio apparatus 6E can communicate with the 3D-WS7 therethrough. The angio apparatus 6E is roughly composed of a support device 11E and a DF system 12.

The support device 11E includes an X-ray tube 21, an X-ray detection unit 22, a C-arm 23, a table-top 25, a high-voltage supply unit 26, a drive mechanism 27, an injector 28, and a pressure detection unit (sensor) 71.

The sensor 71 is disposed to the injector 28 or to a tube for guiding the contrast medium from the injector 28, and the like. The sensor 71 detects a pressure of the contrast medium or a pressure when the contrast medium is injected and supplies a detected signal to a CPU 35a of the DF system 12. The angio apparatus 6E shown in FIG. 16 shows a case that the sensor 71 is disposed in the injector 28.

Note that the components of the X-ray diagnostic system 1E shown in FIG. 16, which are the same as those of the X-ray diagnostic system 1, are denoted by the same reference numerals, and the explanation thereof is omitted.

FIG. 17 is a block diagram showing a function of the sixth embodiment of the X-ray diagnostic system according to the present invention.

FIG. 17 shows a function of the angio apparatus 6E in the function of the X-ray diagnostic system 1E. Since a function of the 3D-WS7 in the function of the X-ray diagnostic system 1E is the same as that explained using FIG. 5, the explanation thereof is omitted.

As shown in FIG. 17, when the CPU 35a (shown in FIG. 16) executes a program, the angio apparatus 6E functions as a pilot image generation unit 64E, a particular region setting unit 42, a delay time setting unit 43E, and a rotation DSA imaging execution unit 44. Further, the delay time setting unit 43E has a contrast imaging start timing setting unit 58 and a delay time calculation unit 59E. Note that although a case that the pilot image generation unit 64E, the particular region setting unit 42, the delay time setting unit 43E, and the rotation DSA imaging execution unit 44 are constructed by software is explained in the embodiment, the embodiment is not limited thereto, and they may be entirely or partly constructed by hardware composed of a circuit and the like.

The pilot image generation unit 64E has a function for applying contrast medium injection start information showing the start of injection of the contrast medium to the contrast image of an $n_b$-th frame generated when it receives the detection signal detected by the sensor 71 (shown in FIG. 16), in addition to the function of the pilot image generation unit 64 (shown in FIG. 13).

The delay time calculation unit 59E has a function for calculating a delay time $T_3$, which employed when the 3D imaging of a particular region is performed, based on the contrast imaging start timing ($n_s/R$) set by the contrast imaging start timing setting unit 58 and the contrast medium injection start timing ($n_b/R$) determined bases on the $n_b$-th frame to which the contrast medium injection start information is applied. For example, the delay time calculation unit 59E calculates the delay time $T_3$, which employed when the 3D imaging of the particular region is performed, using a following equation (3).

$$T_3 = (n_s - n_b)/R \tag{3}$$

Figure 18:
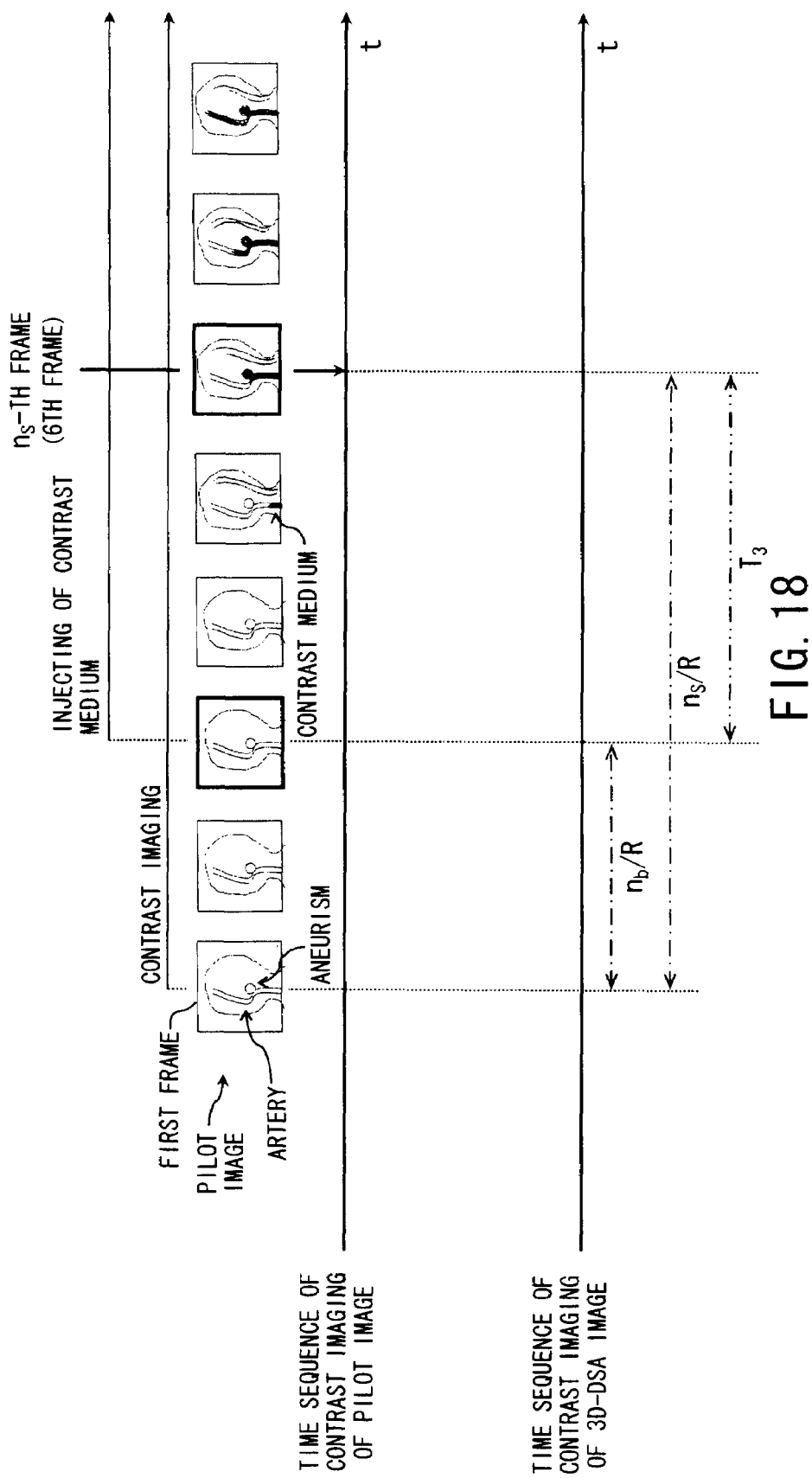
FIG. 18 is a view explaining an equation (3) for calculating a delay time employed when a 3D imaging of a particular region is performed.

FIG. 18 is a view explaining the equation (3) for calculating the delay time $T_3$ when the 3D imaging of the particular region is performed.

An upper part of FIG. 18 shows the time-sequence (t) of the contrast imaging of the pilot images performed to the particular region by the pilot image generation unit 64E and the pilot images. In the contrast imaging of the pilot images, first, the contrast imaging is started at a certain timing and the pilot images are generated, and manual injection of the contrast medium is started at an unknown timing in the midway of the contrast imaging.

A lower part of FIG. 18 is a time-sequence (t) designed based on the upper part and shows the time-sequence (t) of the contrast imaging included in the 3D imaging. The delay time $T_3$, which is employed when the contrast imaging is performed, is calculated by the equation (3) based on a $n_s$-th frame, the $n_b$-th frame to which the contrast medium injection start information is applied, and a frame rate R applied to the image data.

Note that the components of the angio apparatus 6E shown in FIG. 17, which are the same as those of the angio apparatus 6A shown in FIG. 4, are denoted by the same reference numerals, and the explanation thereof is omitted.

Subsequently, an operation of the X-ray diagnostic system 1E of the embodiment will be explained using a flowchart shown in FIG. 19. Note that steps of the flowchart shown in FIG. 19, which are same as those of the flowchart shown in FIG. 7, are denoted by the same reference numerals, and the explanation thereof is omitted.

First, a catheter is inserted into the body of a patient P placed on the table-top 25. When the CPU 35a of the angio apparatus 6E executes the program, the angio apparatus 6E performs mask imaging by controlling a system controller 40, generates the image data of mask images from one direction of a plurality of regions, and stores the image data to a storage unit such as an image memory 32 and the like.

Further, the contrast imaging is started by controlling the system controller 40. After an arbitrary time passes from the start of the contrast imaging, the examiner starts to manually inject the contrast medium. After the start of the contrast imaging, the image data of the contrast image from one direction of the region corresponding to the mask image is generated and stored to the storage unit such as the image memory 32 and the like. Note that the contrast medium injection start information showing the start of injection of the contrast medium is applied to the contrast image of the $n_b$-th frame generated when the detection signal is received from the sensor 71.

Next, the image data of a 2D-DSA image, which is a pilot image as a 2D angiogram, is generated and stored based on the mask image and the contrast image from one direction by controlling an image generating/processing circuit 31, the image memory 32 and the HD 37a (step S41). When mask images and contrast images are generated to the plurality of regions, a pilot image is generated and stored to each of the plurality of regions at step S41.

Next, when a 3D-DSA imaging program is selected, a "delay time setting screen" is displayed on a display device 34a, for example, on a system monitor 34ac (step S42, screen of left edge in FIG. 8). The delay time set to a default value is displayed on the "delay time setting screen".

When the examiner clicks a "confirm" button on the "delay time setting screen", the pilot image of each region which is generated and stored at step S41 is read out and displayed on the display device 34a, for example, on the reference monitor 34ab as a thumbnail image (step S43, second screen from left in FIG. 8). Further, the particular region to which the 3D imaging is performed is set based on the pilot images of the respective regions displayed on the reference monitor 34ab (step S44). Specifically, a region C2 is set as the particular region by the examiner who selects the region C2 from the respective regions (region C1, C2, C3, . . . ) displayed on the reference monitor 34ab using an input device 38a.

Next, the pilot images of the respective frames corresponding to the particular region set at step S44 are time-sequentially displayed on the display device 34a, for example, on the reference monitor 34ab as thumbnail images (step S45, second screen from right in FIG. 8). Further, the pilot image of the $n_s$-th frame corresponding to the start of the contrast imaging is selected based on the pilot images of the respective frames (first frame, second frame, third frame, . . . ) corresponding to the particular region displayed on the reference monitor 34ab. Specifically, the examiner selects the pilot image C2-6 of the $n_s$-th frame, for example, a sixth frame from the pilot images of the respective frames corresponding to the region C as the particular region. Note that the examiner preferably selects a frame in which the contrast medium reaches an interest region (for example, a region where aneurism exists) when a 3D-DSA image is generated.

Further, the contrast imaging start timing, at which the contrast imaging is suitably started, is set based on the selected $n_s$-th frame and the frame rate employed when the pilot image of the particular region is generated. (step S46).

Next, the contrast medium injection start timing, at which the contrast imaging is suitably started is determined based on the $n_s$-th frame, to which the contrast medium injection start information is applied at step S41, and the frame rate employed when the pilot image of the particular region is generated. Then, the delay time, which is employed when the 3D imaging of the particular region is performed, is calculated using the equation (3) based on the contrast medium injection start timing and the contrast imaging start timing set at step S46 (step S47).

The delay time calculated at step S47 is displayed on the display device 34a, for example, on the system monitor 34a (step S8, screen of right edge in FIG. 8). When the examiner pushes an imaging-start switch after a completion of preparations for the 3D imaging, the 3D imaging is started.

According to the X-ray diagnostic system 1E of the embodiment, a 3D-DSA image having improved S/N and a small amount of artifact can be generated and displayed by optimizing the delay time for the 3D imaging while reducing unnecessary exposure of the patient P to the X-ray when the imaging is performed by the rotation DSA imaging execution unit 44. There is in particular a case that a fresh start of the imaging is performed because a manual skill depends on the technology of the examiner by the rotary DSA imaging, but, according to the X-ray diagnostic system 1E of the embodiment, unnecessary exposure of the patient P to the X-ray can be lost by the fresh start. More specifically, according to the X-ray diagnostic system 1E of the embodiment, the accuracy of the X-ray diagnosis can be improved while reducing the unnecessary exposure of the patient P to the X-ray.

Seventh Embodiment

Figure 19:
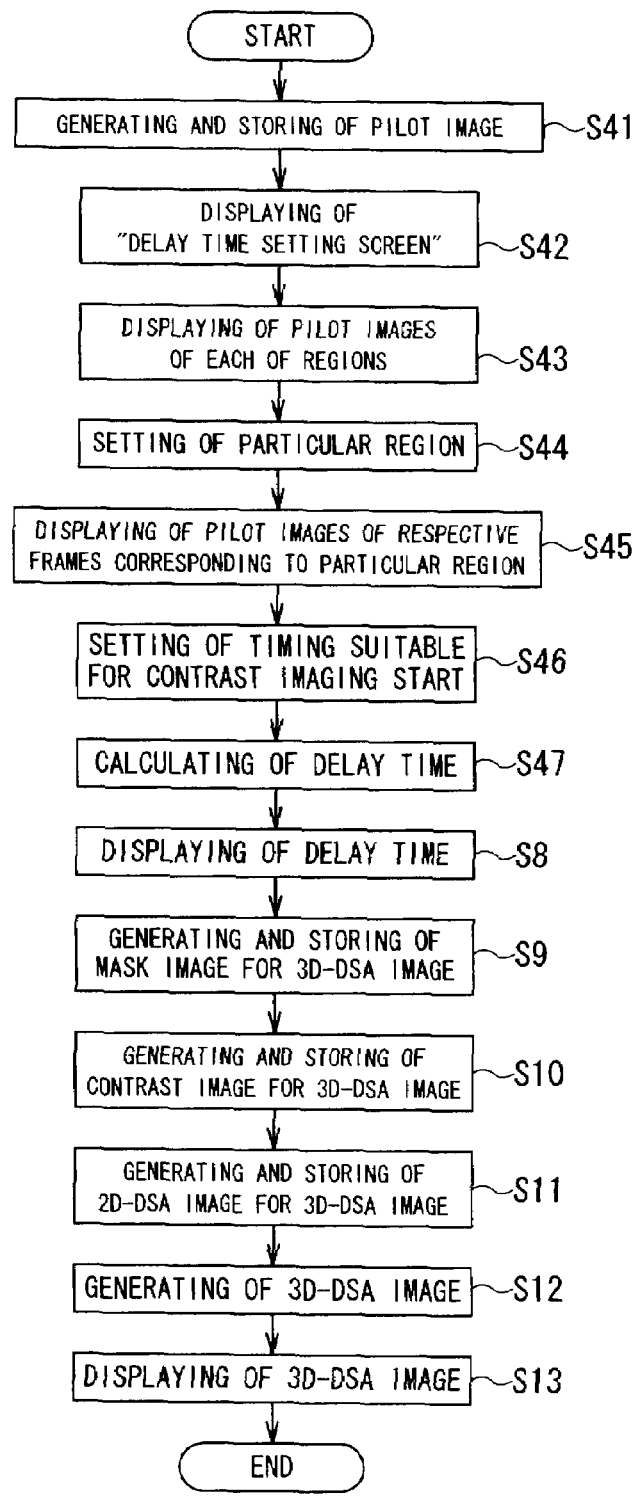
FIG. 19 is a flowchart showing an operation of the diagnostic system of the sixth embodiment.

As shown in FIGS. 5, 16 and 19, an X-ray diagnosis system 1F of a seventh embodiment is composed of an angio apparatus 6F functioning as an X-ray diagnosis apparatus and a 3D-WS7. The X-ray diagnosis system 1F is another embodiment of the X-ray diagnosis system 1E of the sixth embodiment. The X-ray diagnosis system 1F sets a flow time, during which a contrast medium reaches a terminal end of a catheter (a flow-out port of the contrast medium) from an injector 28, to at least each one (region) of the typical length and the typical diameter of the catheter and previously stores the flow time to an HD 37a (shown in FIG. 1) and the like as a default value Df. The X-ray diagnosis system 1F obtains the default value Df of the flow time by inputting at least one of the length and the diameter of the catheter determined depending on a region to which 3D imaging is performed and calculates a delay time $T_4$ using the default value Df of the flow time. Note that the default value Df of the flow time which is set to at least each one of the typical length and the typical diameter of each catheter may be actually measured previously. Further, since at least one of the length and the diameter of the catheter changes depending on a region, it is preferable to set the default value Df to the flow time of each region.

Since the hardware arrangement of the X-ray diagnosis system 1F of the seventh embodiment is the same as that of the X-ray diagnosis system 1E shown in FIG. 16, the explanation thereof is omitted. In contrast, the software arrangement of the X-ray diagnosis system 1F of the seventh embodiment will be explained below.

Figure 20:
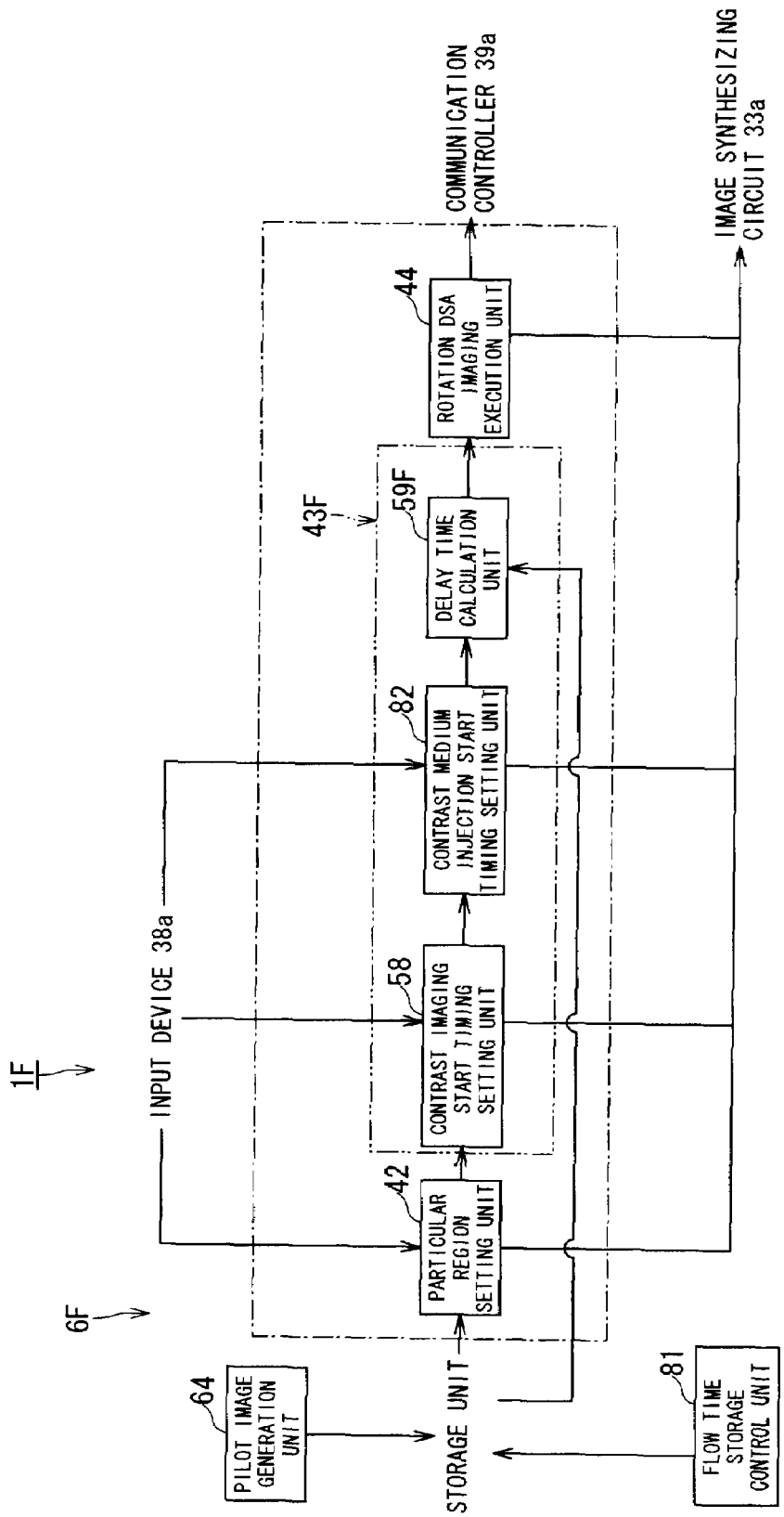
FIG. 20 is a block diagram showing a function of the seventh embodiment of the X-ray diagnostic system according to the present invention.

FIG. 20 is a block diagram showing a function of the seventh embodiment of the X-ray diagnosis system according to the present invention.

FIG. 20 shows a function of the angio apparatus 6F in the function of the X-ray diagnosis system 1F. Note that a function of the 3D-WS7 in the function of the X-ray diagnosis system 1F is the same as that explained using FIG. 5, the explanation thereof is omitted.

As shown in FIG. 20, when a CPU 35a (shown in FIG. 1) executes a program, the angio apparatus 6F functions as a pilot image generation unit 64, a particular region setting unit 42, a delay time setting unit 43F, a rotation DSA imaging execution unit 44, and a flow time storage control unit 81. Further, the delay time setting unit 43F has a contrast imaging start timing setting unit 58, a contrast medium flow-out start timing setting unit 82, and a delay time calculation unit 59F. Note that although a case that the pilot image generation unit 64, the particular region setting unit 42, the delay time setting unit 43F, the rotation DSA imaging execution unit 44, and the flow time storage control unit 81 are constructed by software is explained in the embodiment, the embodiment is not limited thereto, and they may be entirely or partly constructed by hardware composed of a circuit and the like.

The flow time storage control unit 81 has a function for setting the flow time, during which the contrast medium reaches the terminal end of the catheter from the injector 28, to at least each one (region) of the typical length and the typical diameter of the catheter and previously storing the flow time of the contrast medium as the default value Df.

The contrast medium flow-out start timing setting unit 82 has a function for setting a contrast medium flow-out start timing preferable to start the flow-out of the contrast medium for performing the 3D imaging of a particular region based on a particular frame selected the pilot images of respective frames corresponding to the particular region displayed on a reference monitor 34 by the contrast imaging start timing setting unit 58 and a frame rate employed when the pilot image of the particular region is generated. Specifically, the contrast medium flow-out start timing setting unit 82 sets a contrast medium flow-out start timing ($n_c/R$) which corresponds to the start of flow-out of the contrast medium from the terminal end of the catheter based on the pilot image of an $n_c$-th ($n_c<n_s$, $n_c=1, 2, 3, \ldots$) selected from the pilot images of the respective frames corresponding to the particular region and on the frame rate R employed when the pilot image of the particular region is generated.

The delay time calculation unit 59F has a function for calculating the delay time $T_4$ employed when the 3D imaging of the particular region is performed based on the contrast imaging start timing ($n_s/R$) set by the contrast imaging start timing setting unit 58, the contrast medium flow-out start timing ($n_c/R$) set by the contrast medium flow-out start timing setting unit 82, and the default value Df of the flow time stored to the HD 37a and the like. The delay time calculation unit 59F calculates the delay time $T_4$ employed when the 3D imaging of the particular region is performed using a following equation (4).

$$T_4 = Df + (n_s - n_c)/R \qquad (4)$$

Figure 21:
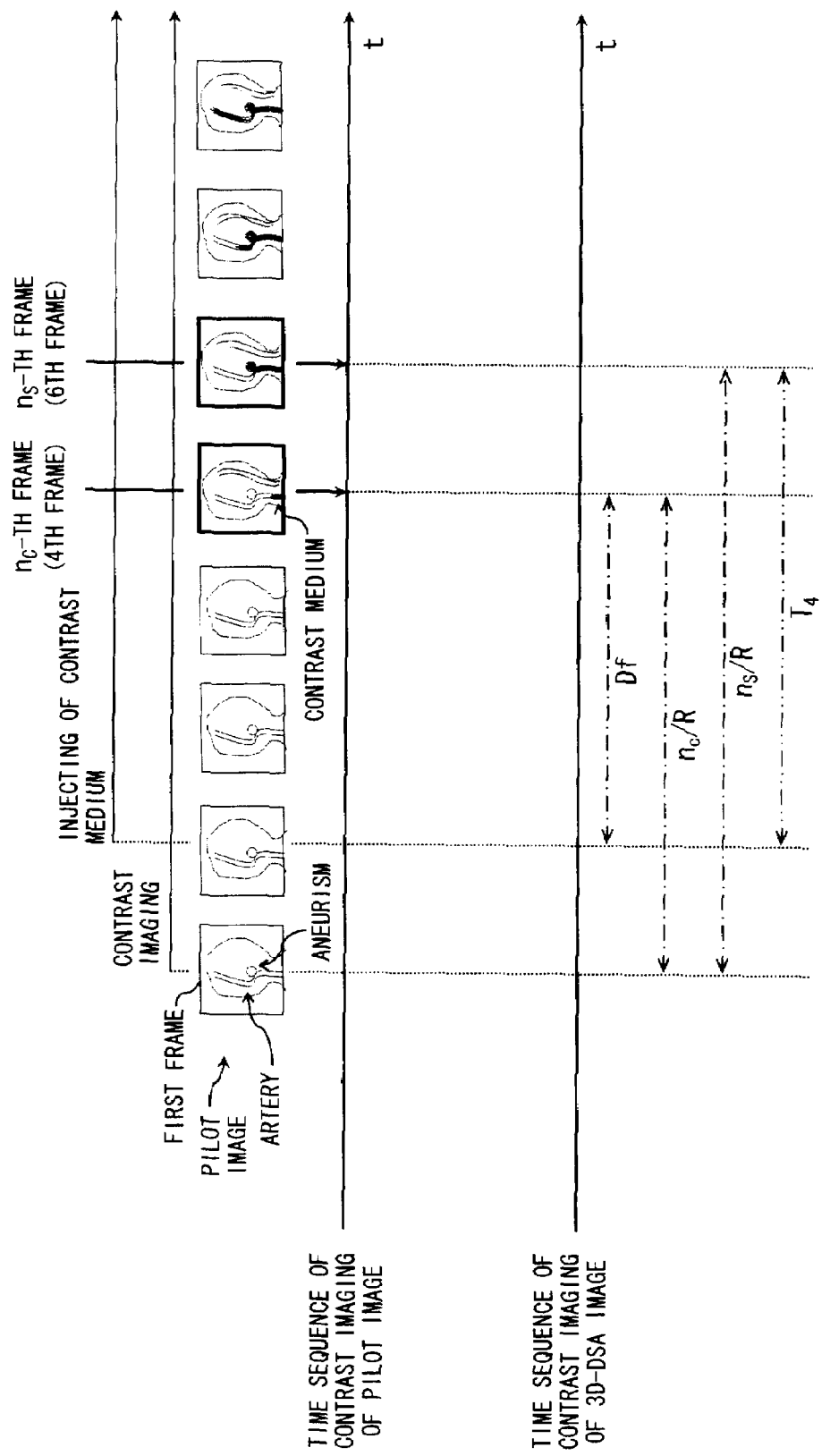
FIG. 21 is a view explaining an equation (4) for calculating a delay time employed when a 3D imaging of a particular region is performed.

FIG. 21 is a view explaining the equation (4) for calculating the delay time $T_4$ employed when the 3D imaging of the particular region is performed.

An upper part of FIG. 21 shows a time sequence (t) of the contrast imaging of the pilot images performed to the particular region generated by the pilot image generation unit 41 and the pilot images. In the contrast imaging of the pilot image, first, the contrast imaging is started at a certain timing, and manual injection of the contrast medium is started at an unknown timing in the midway of the contrast imaging.

A lower part of FIG. 21 is a time-sequence (t) designed based on the upper part and shows the time-sequence (t) of the contrast imaging included in the 3D imaging performed to the particular region. The delay time $T_4$ employed when the contrast imaging is performed is calculated by the equation (4) based on an $n_s$-th frame, an $n_c$-th frame, the default value Df of the flow time, and the frame rate R applied to the image data.

Note that the components of the angio apparatus 6F shown in FIG. 20, which are the same as those of the angio apparatus 6A shown in FIG. 4 and the angio apparatus 6D shown in FIG. 13, are denoted by the same reference numerals, and the explanation thereof is omitted.

Figure 22:
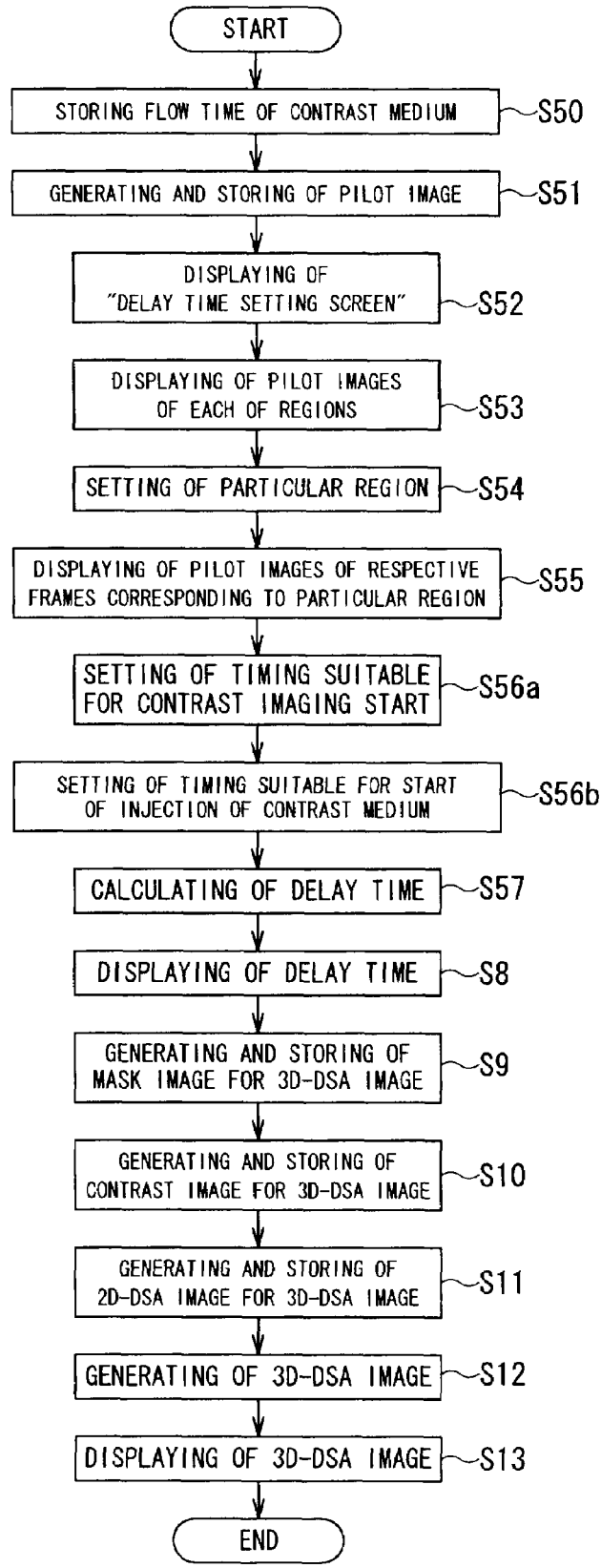
FIG. 22 is a flowchart showing an operation of the diagnostic system of the seventh embodiment.

Subsequently, an operation of the X-ray diagnosis system 1F of the embodiment will be explained using a flowchart shown in FIG. 22. Note that steps of the flowchart shown in FIG. 22, which are same as those of the flowchart shown in FIG. 7, are denoted by the same reference numerals, and the explanation thereof is omitted.

First, the flow time of the contrast medium from an injector 28 to the terminal end of the catheter is set to at least each one (region) of the typical length and the typical diameter of the catheter, and the flow time is previously stored as the default value Df (step S50).

Next, the catheter is inserted in the body of a patient P placed on a table-top 25. When the CPU 35a of the angio apparatus 6F executes the program, the angio apparatus 6F performs mask imaging by controlling a system controller 40, generates the image data of mask images from one direction of a plurality of regions, and causes a storage unit such as an image memory 32 and the like to store the image data.

Further, the angio apparatus 6F starts the contrast imaging by controlling the system controller 40. After an arbitrary time passes from the start of the contrast imaging, an examiner starts to manually inject the contrast medium. After the start of the contrast imaging, the image data of the contrast images from one direction of the region corresponding to the mask image is generated and stored to the storage unit such as the image memory 32 and the like.

Next, the image data of a 2D-DSA image, which is a pilot image as a 2D angiogram, is generated and stored based on the mask image and the contrast image from one direction by controlling an image generating/processing circuit 31, the image memory 32 and the HD 37a (step S51). When mask images and contrast images are generated to the plurality of regions, a pilot image is generated and stored to each of the plurality of regions at step S51.

Next, when a 3D-DSA imaging program is selected, a "delay time setting screen" is displayed on a display device 34a, for example, on a system monitor 34ac (step S52, screen of left edge in FIG. 8). The delay time set to a default value is displayed on the "delay time setting screen".

When the examiner clicks a "confirm" button on the "delay time setting screen", the pilot image of each region which is generated and stored at step S51 is read out and displayed on the display device 34a, for example, on the reference monitor 34ab as a thumbnail image (step S53, second screen from left in FIG. 8). Further, the particular region to which the 3D imaging is performed is set based on the pilot images of the respective regions displayed on the reference monitor 34ab (step S54). Specifically, a region C2 is set as the particular region by the examiner who selects the region C2 from the respective regions (region C1, C2, C3, . . . ) displayed on the reference monitor 34ab using an input device 38a.

Next, the pilot images of the respective frames corresponding to the particular region set at step S54 are time-sequentially displayed on the display device 34a, for example, on the reference monitor 34ab as thumbnail images (step S55, second screen from right in FIG. 8). Further, the pilot image of the $n_s$-th frame corresponding to the start of the contrast imaging is selected based on the pilot images of the respective frames (first frame, second frame, third frame, . . . ) corresponding to the particular region displayed on the reference monitor 34ab. Specifically, the examiner selects the pilot image C2-6 of the $n_s$-th frame, for example, a sixth frame from the pilot images of the respective frames corresponding to the region C as the particular region. Note that the examiner preferably selects a frame in which the contrast medium reaches an interest region (for example, a region where aneurism exists) when a 3D-DSA image is generated.

Further, the contrast imaging start timing, at which the contrast imaging is suitably started, is set based on the selected $n_s$-th frame and the frame rate employed when the pilot image of the particular region is generated (step S56a).

Next, an $n_c$-th frame, which corresponds to the start of injection of the contrast medium, is selected based on the pilot images of the respective frames corresponding to the particular region displayed on the reference monitor 34ab at step S55. Specifically, the examiner selects the pilot image C2-5 of the $n_c$-th frame, for example, a fifth frame suitable for the start of flow-out of the contrast medium from the pilot images of the respective frames corresponding to the region C using the input device 38a. Note that the examiner preferably selects the first frame in which the contrast medium appears on the pilot image.

Further, the contrast medium flow-out start timing suitable to the start of flow-out of the contrast medium is set based on the selected $n_c$-th frame and the frame rate employed when the pilot image of particular region is generated (step S56b).

Next, the delay time, which is employed when the 3D imaging of the particular region is performed, is calculated using the equation (4) based on the contrast imaging start timing set step S56a, the contrast medium flow-out start timing set at step S56b, and the default value Df of the flow time stored at step S50 (step S57).

The delay time calculated at step S57 is displayed on the display device 34a, for example, on the system monitor 34ac (step S8, screen of right edge in FIG. 8). When the examiner pushes an imaging-start switch after a completion of preparations for the 3D imaging, the 3D imaging is started.

Note that, to set a more correct delay time, it is sufficient to cause the terminal end of the catheter to appear on the displayed pilot image at step S56b. In this case, it is sufficient for the examiner to select the first frame in which the contrast medium appears to the terminal end of the catheter on the displayed pilot image.

According to the X-ray diagnostic system 1F of the embodiment, a 3D-DSA image having improved S/N and a small amount of artifact can be generated and displayed by optimizing the delay time for the 3D imaging while reducing unnecessary exposure of the patient P to the X-ray when the imaging is performed by the rotation DSA imaging execution unit 44. There is in particular a case that a fresh start of the imaging is performed because a manual skill depends on the technology of the examiner by the rotary DSA imaging, but, according to the X-ray diagnostic system 1F of the embodiment, unnecessary exposure of the patient P to the X-ray can be lost by the fresh start. More specifically, according to the X-ray diagnostic system 1F of the embodiment, the accuracy of the X-ray diagnosis can be improved while reducing the unnecessary exposure of the patient P to the X-ray.

What is claimed is:

1. An X-ray diagnostic system comprising:
   a display unit configured to display images of a plurality of frames collected at a predetermined frame rate about an object;
   a selection unit configured to select an image of a particular frame from the images of the frames displayed on the display unit;
   a calculation unit configured to calculate a delay time for a three-dimensional imaging to the particular frame selected by the selection unit based on the frame rate; and
   an imaging execution unit configured to execute imaging based on the delay time calculated by the calculation unit,
   wherein the calculation unit calculates the delay time $T_1$ for the three-dimensional imaging according to the following equation, by using a contrast imaging start timing ($n_s/R$) based on an $n_s$-th ($n_s$=1, 2, 3, . . . ) frame as the particular frame and the predetermined frame rate R, and a delay time $T_0$ employed when the images have been collected, $$T_1 = T_0 + n_s/R.$$

2. An X-ray diagnostic system according to claim 1, further comprising:
   a particular region setting unit configured to set a particular region by selecting a predetermined frame among the frames every region of the object,
   wherein the display unit displays the images of the frames every region.

3. An X-ray diagnostic system according to claim 2, wherein the display unit displays the images of the frames every frame corresponding to the particular region, the selection unit selects the particular frame among the frames corresponding to the particular region.

4. An X-ray diagnostic system comprising:
   a display unit configured to display images of a plurality of frames collected at a predetermined frame rate about an object;
   a selection unit configured to select an image of a particular frame from the images of the frames displayed on the display unit;
   a calculation unit configured to calculate a delay time for a three-dimensional imaging to the particular frame selected by the selection unit based on the frame rate;
   a storage unit configured to store the delay time for the three-dimensional imaging, calculated by the calculation unit, with a first generating condition; and
   an imaging execution unit configured to execute the three-dimensional imaging based on the delay time for the three-dimensional imaging corresponding to the first generating condition, when a second generating condition, set after the delay time have been stored, accords with the first generating condition.

5. An X-ray diagnostic system according to claim 4, further comprising:
   a fluoroscopic time setting unit configured to set a fluoroscopic time less than the delay time for the three-dimensional imaging,
   wherein the imaging execution unit performs fluoroscopy and displays a fluoroscopic image by the display unit during the fluoroscopic time, which is generated by and supplied from the fluoroscopic time setting unit from a start of injection of a contrast medium until a contrast imaging start signal is input, and contrast imaging is started when the contrast imaging start signal is input.

6. An X-ray diagnostic system according to claim 4, wherein the generating condition is at least one of an examiner, the object and a region of the object.

7. An X-ray diagnostic system according to claim 4, further comprising:
   a particular region setting unit configured to set a particular region by selecting a predetermined frame among the frames every region of the object,
   wherein the display unit displays the images of the frames every region.

8. An X-ray diagnostic system comprising:
   a display unit configured to display images of a plurality of frames collected at a predetermined frame rate about an object;
   a selection unit configured to select an image of a particular frame from the images of the frames displayed on the display unit;
   a calculation unit configured to calculate a delay time for a three-dimensional imaging to the particular frame selected by the selection unit based on the frame rate; and
   an imaging execution unit configured to execute imaging based on the delay time calculated by the calculation unit, wherein the selection unit selects the particular frame and a frame before the particular frame based on the displaying by the display unit, the calculation unit calculates the delay time for the three-dimensional imaging by setting a contrast imaging start timing for the three-dimensional imaging based on the particular frame and the predetermined frame rate, and by setting a contrast medium injection start timing for the three-dimensional imaging based on the frame before the particular frame and the predetermined frame rate.

9. An X-ray diagnostic system according to claim 8, wherein the calculation unit calculates a delay time $T_2$ for the three-dimensional imaging according to the following equation, by using a contrast imaging start timing ($n_s/R$) based on an $n_s$-th ($n_s=1, 2, 3, \ldots$) frame as the particular frame and the predetermined frame rate R, and the contrast medium injection start timing ($n_a/R$) based on an $n_a$-th ($n_a=1, 2, 3, \ldots$) frame as the frame before the particular frame and the predetermined frame rate R, $$T_2 = (n_s - n_a)/R.$$

10. An X-ray diagnostic system according to claim 8, further comprising:
a particular region setting unit configured to set a particular region by selecting a predetermined frame among the frames every region of the object,
wherein the display unit displays the images of the frames every region.

11. An X-ray diagnostic system comprising:
a display unit configured to display images of a plurality of frames collected at a predetermined frame rate about an object;
a selection unit configured to select an image of a particular frame from the images of the frames displayed on the display unit;
a calculation unit configured to calculate a delay time for a three-dimensional imaging to the particular frame selected by the selection unit based on the frame rate;
an imaging execution unit configured to execute imaging based on the delay time calculated by the calculation unit,
a pressure detection unit configured to detect a pressure of a contrast medium or a pressure when the contrast medium is injected; and
an information applying unit configured to apply contrast medium injection start information, showing a start of a injection of the contrast medium, to a frame generated when it receives a detection signal detected by the pressure detection unit,
wherein the selection unit selects the particular frame based on the displaying by the display unit and selects a frame, to which is applied the contrast medium injection start information by the information applying unit, before the particular frame, and the calculation unit calculates the delay time for the three-dimensional imaging by setting a contrast imaging start timing for the three-dimensional imaging based on the particular frame and the predetermined frame rate, and by setting a contrast medium injection start timing for the three-dimensional imaging based on the frame before the particular frame and the predetermined frame rate.

12. An X-ray diagnostic system according to claim 11, wherein the pressure detection unit is arranged on an injector or a position to a tube for guiding the contrast medium from the injector.

13. An X-ray diagnostic system according to claim 11, wherein the calculation unit calculates a delay time $T_3$ for the three-dimensional imaging according to the following equation, by using a contrast imaging start timing ($n_s/R$) based on an $n_s$-th ($n_s=1, 2, 3, \ldots$) frame as the particular frame and the predetermined frame rate R, and the contrast medium injection start timing ($n_b/R$) based on an $n_b$-th ($n_b=1, 2, 3, \ldots$) frame as the frame before the particular frame and the predetermined frame rate R, $$T_3 = (n_s - n_b)/R.$$

14. An X-ray diagnostic system according to claim 11, further comprising:
a particular region setting unit configured to set a particular region by selecting a predetermined frame among the frames every region of the object,
wherein the display unit displays the images of the frames every region.

15. An X-ray diagnostic system comprising:
a display unit configured to display images of a plurality of frames collected at a predetermined frame rate about an object;
a selection unit configured to select an image of a particular frame from the images of the frames displayed on the display unit;
a calculation unit configured to calculate a delay time for a three-dimensional imaging to the particular frame selected by the selection unit based on the frame rate;
an imaging execution unit configured to execute imaging based on the delay time calculated by the calculation unit, and
a storage unit configured to store a flow time of a contrast medium as a default value, during which the contrast medium reaches a terminal end of a catheter from an injector,
wherein the selection unit selects the particular frame and a frame before the particular frame based on the displaying by the display unit, the calculation unit calculates the delay time for the three-dimensional imaging based on the default value of the flow time, a contrast imaging start timing and a contrast medium flow-out start timing, by setting the contrast imaging start timing for the three-dimensional imaging based on the particular frame and the predetermined frame rate, and by setting the contrast medium flow-out start timing suitable to the start of flow-out of the contrast medium for the three-dimensional imaging based on the frame before the particular frame and the predetermined frame rate.

16. An X-ray diagnostic system according to claim 15, wherein the calculation unit calculates a delay time $T_3$ for the three-dimensional imaging according to the following equation, by using a contrast imaging start timing ($n_s/R$) based on an $n_s$-th ($n_s=1, 2, 3, \ldots$) frame as the particular frame and the predetermined frame rate R, the contrast medium flow-out start timing ($n_c/R$) based on an $n_c$-th ($n_c=1, 2, 3, \ldots$) frame as the frame before the particular frame and the predetermined frame rate R, and the default value Df of the flow time, $$T_3 = D_f + (n_s - n_c)/R.$$

17. An X-ray diagnostic system according to claim 15, wherein, the storage unit stores the flow time at least each one of a length and a diameter of the catheter.

18. An X-ray diagnostic system according to claim 15, further comprising:
a particular region setting unit configured to set a particular region by selecting a predetermined frame among the frames every region of the object,
wherein the display unit displays the images of the frames every region.

* * * * *